(12) United States Patent
Narimatsu

(10) Patent No.: US 6,190,325 B1
(45) Date of Patent: Feb. 20, 2001

(54) BLOOD-PRESSURE MONITORING APPARATUS

(75) Inventor: Kiyoyuki Narimatsu, Kasugai (JP)

(73) Assignee: Colin Corporation, Komaki (JP)

( * ) Notice: Under 35 U.S.C. 154(b), the term of this patent shall be extended for 0 days.

(21) Appl. No.: 09/392,733

(22) Filed: Sep. 9, 1999

(30) Foreign Application Priority Data

Oct. 2, 1998 (JP) .................................................. 10-281050

(51) Int. Cl.[7] ...................................................... A61B 5/00
(52) U.S. Cl. .......................... 600/490; 600/485; 600/494; 600/500
(58) Field of Search .................................... 600/483, 485, 600/481, 490, 492, 495, 500, 502, 526

(56) References Cited

U.S. PATENT DOCUMENTS

| | | | |
|---|---|---|---|
| 5,671,750 | * | 9/1997 | Shinoda ............................ 600/485 X |
| 5,738,612 | * | 4/1998 | Tsuda ............................... 600/485 X |
| 5,776,071 | * | 7/1998 | Inukai et al. ...................... 600/485 X |
| 5,876,348 | * | 3/1999 | Sugo et al. ........................ 600/485 X |
| 5,906,581 | * | 5/1999 | Tsuda ............................... 600/490 X |
| 6,007,492 | * | 12/1999 | Goto et al. ........................ 600/485 |

* cited by examiner

Primary Examiner—Cary O'Connor
Assistant Examiner—Ryan Carter
(74) Attorney, Agent, or Firm—Oliff & Berridge PLC.

(57) ABSTRACT

A blood-pressure monitoring apparatus including a measuring device which includes an inflatable cuff adapted to apply a pressing pressure to a body portion of a living subject and which measures at least one blood-pressure value of the living subject by changing the pressing pressure of the inflatable cuff, a blood-pressure-relating-value calculating device for iteratively calculating a blood-pressure-relating value relating to the blood pressure of the living subject, a starting device for starting, when a value based on the calculated blood-pressure-relating value satisfies a predetermined first condition, a blood-pressure measurement of the measuring device, a circulatory-system-relating information obtaining device which obtains a circulatory-system-relating information relating to a circulatory system of the living subject, and a condition changing device for changing, when the obtained circulatory-system-relating information satisfies a predetermined second condition, the predetermined first condition to a changed first condition which at least one of respective values based on a plurality of blood-pressure-relating values calculated by the blood-pressure-relating-value calculating device earlier satisfies than satisfying the predetermined first condition so that the starting device earlier starts the blood-pressure measurement of the measuring device.

21 Claims, 10 Drawing Sheets

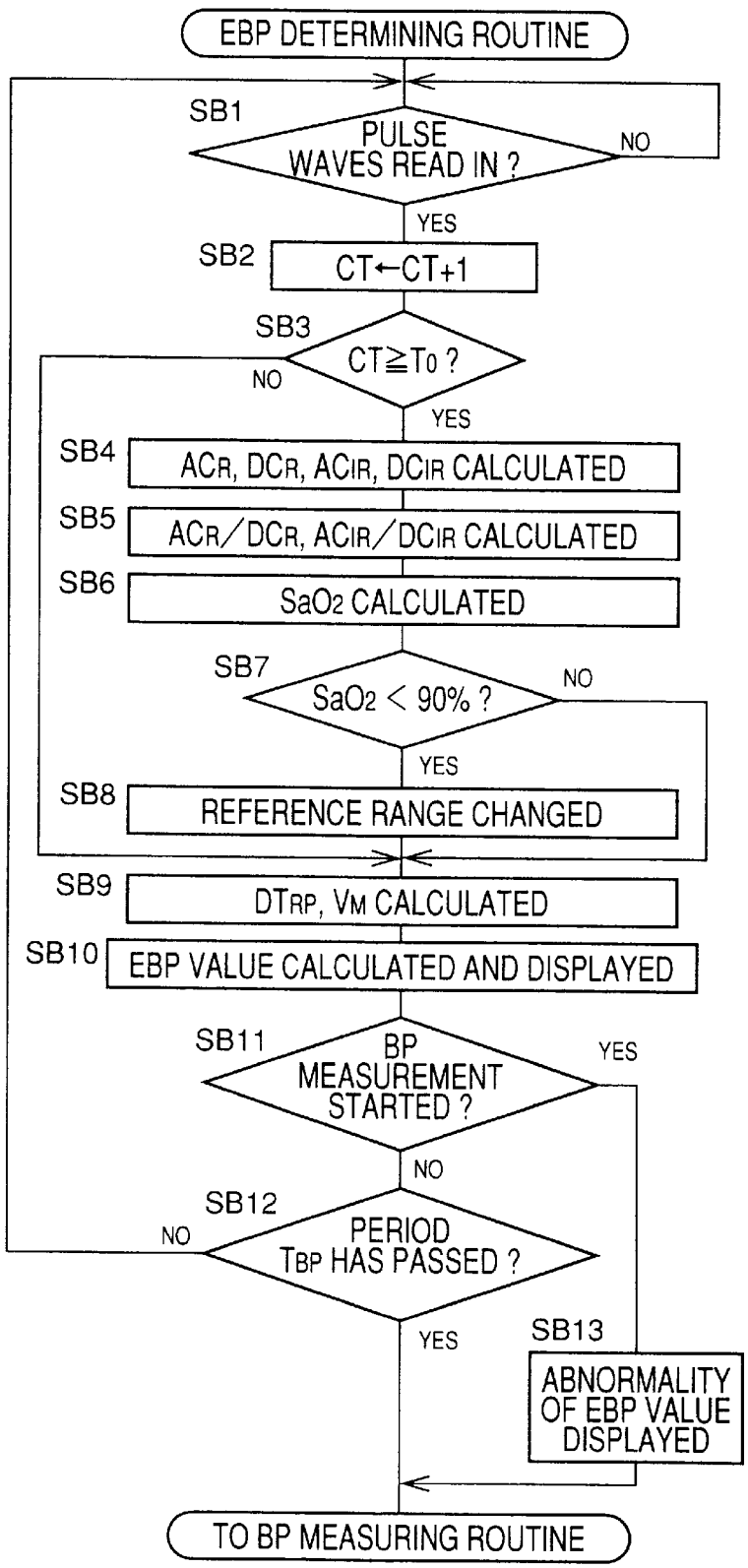

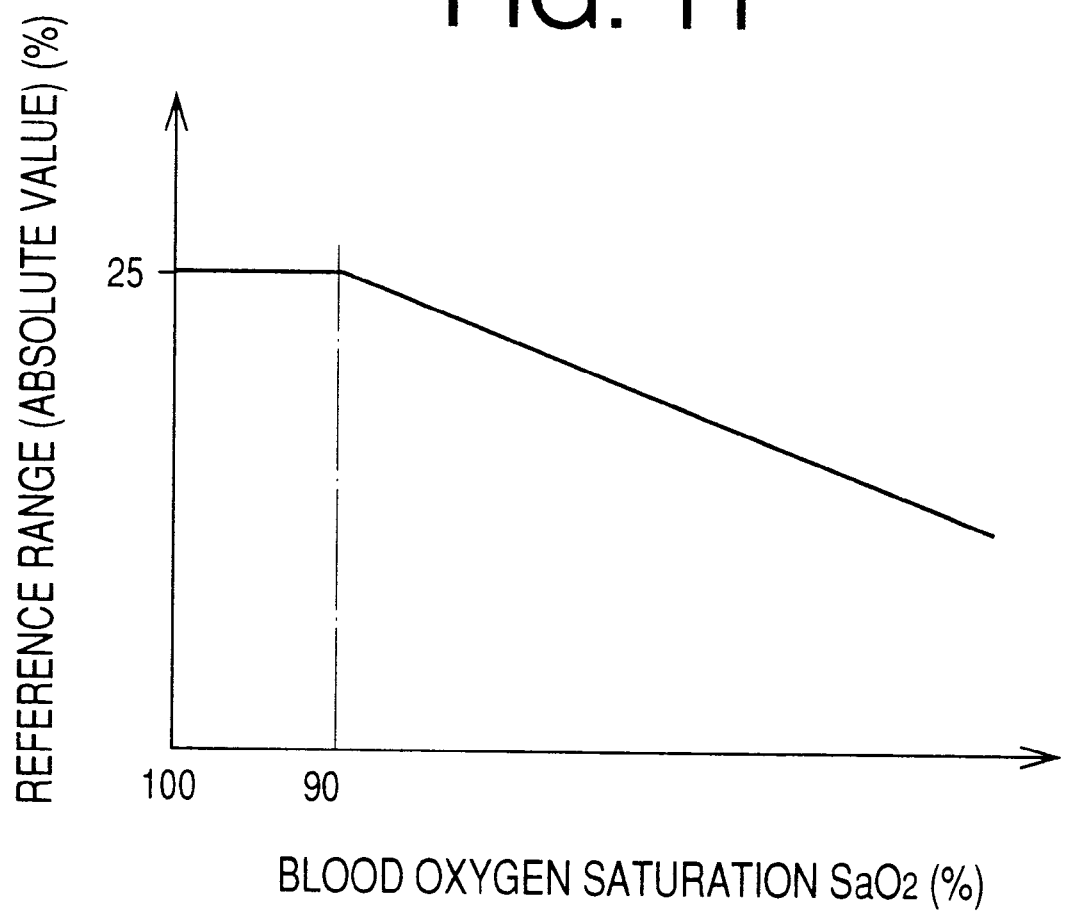

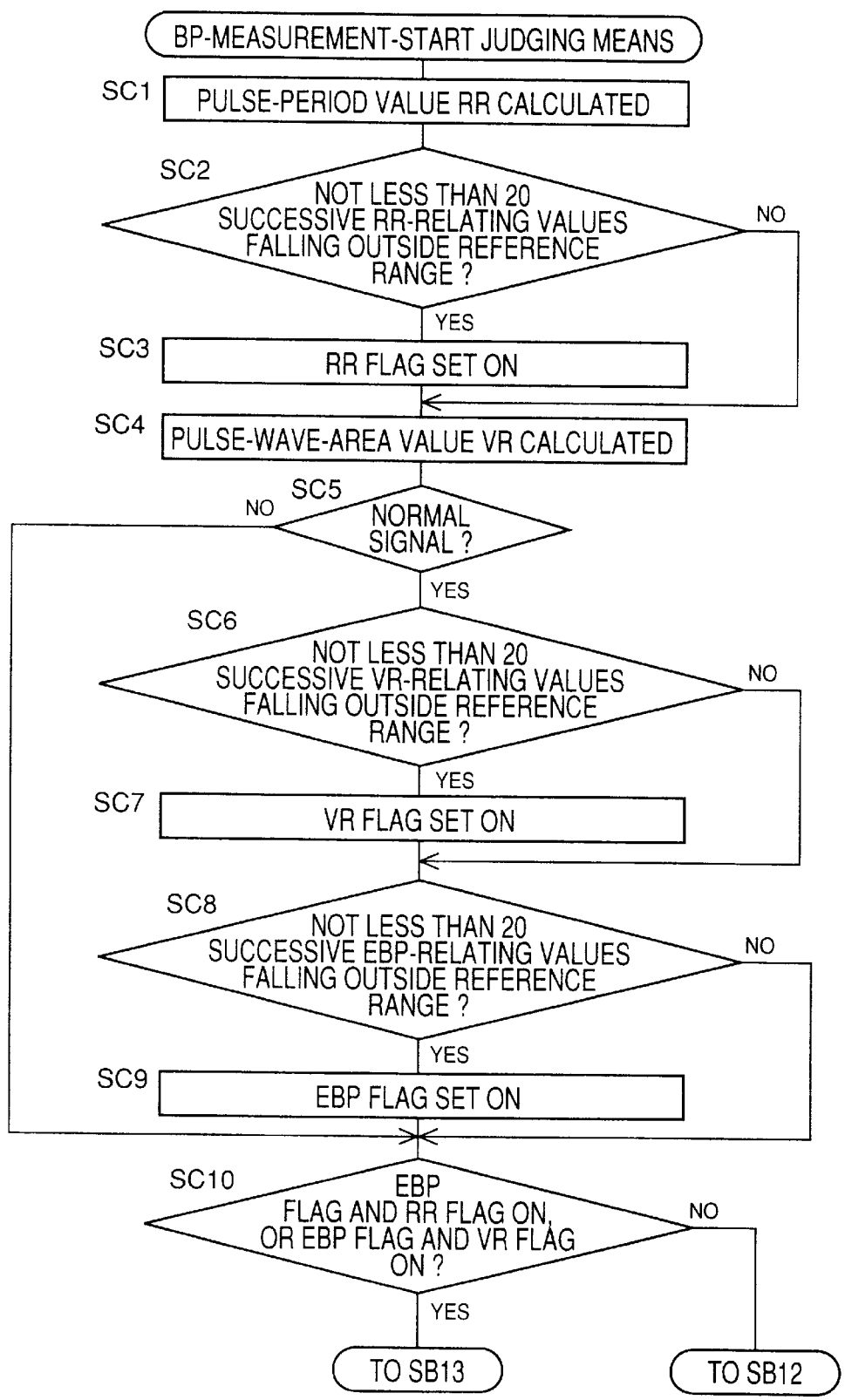

BLOOD-PRESSURE MONITORING APPARATUS

BACKGROUND OF THE INVENTION

1. Field of the Invention

The present invention relates to a blood-pressure monitoring apparatus which monitors a blood pressure of a living subject.

2. Related Art Statement

As information relating to a pulse wave which propagates through an arterial vessel of a living subject, there are known a pulse-wave-propagation time DT and a pulse-wave-propagation velocity $V_M$ (m/s). The pulse-wave-propagation time DT is a time which is needed by a pulse wave to propagate between two different positions of the arterial vessel. Additionally, it is known that the above pulse-wave-propagation-relating information is, within a predetermined range, substantially proportional to the blood pressure ("BP", mmHg) of the living subject. Therefore, there has been proposed a BP monitoring apparatus which determines, in advance, coefficients a, B in the following expression: $EBP=\alpha(DT)+\beta$ (where $\alpha$ is a negative constant and $\beta$ is a positive constant), or $EBP=\alpha(V_M)+\beta$ (where a and $\beta$ are positive constants), based on two measured BP values of the subject and two measured pulse-wave-propagation time values (DT) or two measured pulse-wave-propagation velocity values ($V_M$), iteratively determines an estimated BP value EBP of the subject, based on each set of subsequently obtained pulse-wave-propagation-relating information, according to the above-indicated first or second expression, and starts a BP measurement using an inflatable cuff when an abnormal estimated BP value EBP is determined. An example of the BP monitoring apparatus is disclosed in U.S. Pat. No. 5,752,920.

Meanwhile, the elasticity or flexibility of blood vessels of a patient as a living subject may be lost due to arteriosclerosis or temporary constriction of the blood vessels. In this case, the BP of the patient cannot be easily controlled. Therefore, it is needed to quickly measure a BP value of the patient and quickly make a decision about whether or not any treatments should be given to the patient. This is also the case with a patient who has fallen in shock because of excessive expansion of the blood vessels upon administration of a hypotensive drug.

In addition, a relationship between pulse-wave-propagation-relating information and estimated BP value EBP changes depending upon a hardness of a blood vessel for which the pulse-wave-propagation-relating information is obtained. That is, the coefficient $\alpha$ of each of the above-indicated two expressions that defines the relationship between pulse-wave-propagation-relating information and estimated BP value EBP changes depending upon the hardness of the blood vessel. Therefore, if the hardness of the blood vessel largely changes while estimated BP values EBP are iteratively determined for monitoring the BP of the patient, the accuracy of the estimated BP values EBP decreases, which may lead to delaying commencement of a BP measurement using the inflatable cuff.

SUMMERY OF THE INVENTION

It is therefore an object of the present invention to provide a blood-pressure monitoring apparatus which early starts a blood-pressure measurement using an inflatable cuff, when information relating to the circulatory system of a living subject satisfies a predetermined condition.

The present invention provides a blood-pressure monitoring apparatus which has one or more of the technical features that are described below in respective paragraphs given parenthesized sequential numbers (1) to (21). Any technical feature which includes another technical feature shall do so by referring, at the beginning, to the parenthesized sequential number given to that technical feature.

(1) According to a first feature of the present invention, there is provided a blood-pressure monitoring apparatus comprising a measuring device which includes an inflatable cuff adapted to apply a pressing pressure to a body portion of a living subject and which measures at least one blood-pressure value of the living subject by changing the pressing pressure of the inflatable cuff; a pulse-wave-propagation-relating-information obtaining device which iteratively obtains a piece of pulse-wave-propagation-relating information relating to propagation of a pulse wave through an arterial vessel of the living subject; estimating means for iteratively estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure; starting means for starting, when a value based on the estimated blood-pressure value does not fall within a predetermined first range, a blood-pressure measurement of the measuring device; index-value calculating means for calculating, based on the at least one blood-pressure value of the living subject measured by the measuring device, an index value indicative of a hardness of a blood vessel of the living subject; and range changing means for changing, when the calculated index value does not fall within a predetermined second range, the predetermined first range to a changed first range which is contained in the predetermined first range and is narrower than the predetermined first range. In the present blood-pressure ("BP") monitoring apparatus, the range changing means changes, when the calculated index value does not fall within the predetermined second range, the predetermined first range to the changed first range which is contained in the predetermined first range and is narrower than the predetermined first range. Thus, the starting means can earlier start the blood-pressure measurement of the measuring device. For example, in the case where the elasticity or flexibility of blood vessels of the living subject has been lost or the blood vessels of the subject are excessively expanded, the measuring device can earlier measure a BP value of the subject.

(2) According to a second feature of the present invention that includes the first feature (1), the blood-pressure monitoring apparatus further comprises relationship determining means for determining the relationship between pulse-wave-propagation-relating information and blood pressure, based on at least one blood- pressure value of the living subject measured by the measuring device and at least one piece of pulse-wave-propagation-relating information obtained by the pulse-wave-propagation-relating information obtaining device.

(3) According to a third feature of the present invention, there is provided a blood-pressure monitoring apparatus comprising a measuring device which includes an inflatable cuff adapted to apply a pressing pressure to a body portion of a living subject and which measures at least one blood-pressure value of the living subject by changing the pressing pressure of the inflatable cuff; a pulse-wave-propagation-relating-information obtaining device which iteratively obtains a piece of pulse-wave-propagation-relating information relating to propagation of a pulse wave through an arterial vessel of the living subject; estimating means for iteratively estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure; starting means for starting, when a value based on to the estimated blood-pressure value does not fall within a predetermined first range, a blood-pressure measurement of the measuring device; index-value calculating means for calculating, based on the at least one blood-pressure value of the living subject measured by the measuring device, an index value indicative of a hardness of a blood vessel of the living subject; change-value calculating means for calculating a change value relating to a change of a first index value calculated by the index-value calculating means from a second index value calculated prior to the first index value by the index-value calculating means; and range changing means for changing, when the calculated change value does not fall within a predetermined second range, the predetermined first range to a changed first range which is contained in the predetermined first range and is narrower than the predetermined first range. In the present BP monitoring apparatus, the range changing means changes, when the calculated change value does not fall within the predetermined second range, the predetermined first range to the changed first range which is contained in the predetermined first range and is narrower than the predetermined first range. Thus, the starting means can earlier start the blood-pressure measurement of the measuring device. For example, in the case where the hardness of blood vessels of the living subject largely changes and the accuracy of the estimated BP value or values decreases during the monitoring of BP of the living subject, the measuring device can earlier measure a BP value of the subject.

(4) According to a fourth feature of the present invention, there is provided a blood-pressure monitoring apparatus comprising a measuring device which includes an inflatable cuff adapted to apply a pressing pressure to a first body portion of a living subject and which measures at least one blood-pressure value of the living subject by changing the pressing pressure of the inflatable cuff; a pulse-wave-propagation-relating-information obtaining device which iteratively obtains a piece of pulse-wave-propagation-relating information relating to propagation of a pulse wave through an arterial vessel of the living subject; estimating means for iteratively estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure; starting means for starting, when a value based on the estimated blood-pressure value does not fall within a predetermined range, a blood-pressure measurement of the measuring device; a photoelectric-pulse-wave obtaining device which is adapted to be worn on a second body portion of the living subject, and which emits, toward the second body portion, a first light exhibiting different absorption factors with respect to oxygenated hemoglobin and reduced hemoglobin, respectively, and a second light exhibiting substantially same absorption factors with respect to the oxygenated hemoglobin and the reduced hemoglobin, respectively, and obtains a first and a second photoelectric pulse wave from the first and second lights received from the second body portion, respectively; blood-oxygen-saturation calculating means for calculating, based on the obtained first and second photoelectric pulse waves, a blood oxygen saturation value of the second body portion of the living subject; and range changing means for changing, when the calculated blood oxygen saturation value is smaller than a predetermined value, the predetermined range to a changed range which is contained in the predetermined range and is narrower than the predetermined range, the range changing means determining the changed range based on a difference between the calculated blood oxygen saturation value and the predetermined value. In the present BP monitoring apparatus, the range changing means changes, when the calculated blood oxygen saturation value is smaller than the predetermined value, the predetermined range to the changed range which is contained in the predetermined range and is narrower than the predetermined range, and determines the changed range based on the difference between the calculated blood oxygen saturation value and the predetermined value. Thus, the starting means can earlier start the blood-pressure measurement of the measuring device, by a time corresponding to the degree of abnormality of the blood oxygen saturation of the living subject. The oxygen saturation of blood of a peripheral blood vessel of the subject may decrease prior to the change of BP of the subject, when the hardness of the blood vessel largely changes. Thus, the measuring device can earlier measure a BP value of the subject.

(5) According to a fifth feature of the present invention, there is provided a blood-pressure monitoring apparatus comprising a measuring device which includes an inflatable cuff adapted to apply a pressing pressure to a first body portion of a living subject and which measures at least one blood-pressure value of the living subject by changing the pressing pressure of the inflatable cuff; blood-pressure-relating-value calculating means for iteratively calculating a blood-pressure-relating value relating to the blood pressure of the living subject; starting means for starting, when a value based on the calculated blood-pressure-relating value satisfies a predetermined first condition, a blood-pressure measurement of the measuring device; a circulatory-system-relating information obtaining device which obtains a circulatory-system-relating information relating to a circulatory system of the living subject; and condition changing means for changing, when the obtained circulatory-system-relating information satisfies a predetermined second condition, the predetermined first condition to a changed first condition which at least one of respective values based on a plurality of blood-pressure-relating values calculated by the blood-pressure-relating-value calculating means earlier satisfies than satisfying the predetermined first condition so that the starting means earlier starts the blood-pressure measurement of the measuring device. In the present BP monitoring apparatus, the range changing means changes, when the obtained circulatory-system-relating information satisfies the predetermined second condition, the predetermined first condition to the changed first condition which at least one of respective values based on a plurality of blood-pressure-relating values calculated by the blood-pressure-relating-value calculating means earlier satisfies than satisfying the predetermined first condition. Thus, the starting means earlier starts the blood-pressure measurement of the measuring device, and the measuring device can earlier measure a BP value of the subject.

(6) According to a sixth feature of the present invention that includes the fifth feature (5), the starting means comprises means for starting the blood-pressure measurement of the measuring device, when the value based on the calculated blood-pressure-relating value satisfies the predetermined first condition selected from the group consisting of (a) the value based on the calculated blood-pressure-relating value does not fall within a predetermined first range, (b) the value based on the calculated blood-pressure-relating value is greater than a predetermined first value, and (c) the value based on the calculated blood-pressure-relating value is smaller than a predetermined second value.

(7) According to a seventh feature of the present invention that includes the sixth feature (6), the condition changing means comprises means for changing the predetermined first condition to the changed first condition selected from the group consisting of (d) the at least one of the respective values based on the plurality of blood-pressure-relating values does not fall within a changed first range which is contained in the predetermined first range and is narrower than the predetermined first range, (e) the at least one of the respective values based on the plurality of blood-pressure-relating values is greater than a changed first value smaller than the predetermined first value, and (f) the at least one of the respective values based on the plurality of blood-pressure-relating values is smaller than a changed second value greater than the predetermined second value.

(8) According to an eighth feature of the present invention that includes the seventh feature (7), the circulatory-system-relating-information obtaining device comprises index-value calculating means for calculating, based on the at least one blood-pressure value of the living subject measured by the measuring device, an index value indicative of a hardness of a blood vessel of the living subject, and wherein the condition changing means comprises means for changing the predetermined first condition to the changed first condition, when the calculated index value satisfies the predetermined second condition selected from the group consisting of (g) the calculated index value does not fall within a predetermined second range, (h) the calculated index value is greater than a predetermined third value, and (i) the calculated index value is smaller than a predetermined fourth value.

(9) According to a ninth feature of the present invention that includes the eighth feature (8), the blood-pressure-relating value calculating means comprises a pulse-wave-propagation-relating-information obtaining device which iteratively obtains a piece of pulse-wave-propagation-relating information relating to propagation of a pulse wave through an arterial vessel of the living subject; and estimating means for estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure, and the index-value calculating means comprises means for calculating the index value indicative of the hardness of the blood vessel of the living subject, based on the blood-pressure value of the subject measured by the measuring device and the piece of pulse-wave-propagation-relating information obtained by the pulse-wave-propagation-relating-information obtaining device when the blood-pressure value of the subject is measured by the measuring device. In this case, since the index-value calculating means calculates the index value based on the pulse-wave-propagation-relating information that is used by the estimating means for estimating the blood-pressure value of the living subject, the calculated index value enjoys the accuracy of the pulse-wave-propagation-relating information.

(10) According to a tenth feature of the present invention that includes any one of the seventh to ninth features (7) to (9), the circulatory-system-relating-information obtaining device comprises index-value calculating means for calculating, based on the at least one blood-pressure value of the living subject measured by the measuring device, an index value indicative of a hardness of a blood vessel of the living subject; and change-value calculating means for calculating a change value relating to a change of a first index value calculated by the index-value calculating means from a second index value calculated prior to the first index value by the index-value calculating means, and the condition changing means comprises means for changing the predetermined first condition to the changed first condition, when the calculated change value satisfies the predetermined second condition selected from the group consisting of (g) the calculated change value does not fall within a predetermined second range, (h) the calculated change value is greater than a predetermined third value, and (i) the calculated change value is smaller than a predetermined fourth value.

(11) According to an eleventh feature of the present invention that includes any one of the seventh to tenth features (7) to (10), the circulatory-system-relating-information obtaining device comprises a photoelectric-pulse-wave obtaining device which is adapted to be worn on a second body portion of the living subject, and which emits, toward the second body portion, a first light exhibiting different absorption factors with respect to oxygenated hemoglobin and reduced hemoglobin, respectively, and a second light exhibiting substantially same absorption factors with respect to the oxygenated hemoglobin and the reduced hemoglobin, respectively, and obtains a first and a second photoelectric pulse wave from the first and second lights received from the second body portion, respectively; and blood-oxygen-saturation calculating means for calculating, based on the obtained first and second photoelectric pulse waves, a blood oxygen saturation value of the second body portion of the living subject; and the condition changing means comprises means for changing the predetermined first condition to the changed first condition, when the calculated blood oxygen saturation value satisfies the predetermined second condition that the calculated blood oxygen saturation value is smaller than a predetermined third value.

(12) According to a twelfth feature of the present invention that includes the eleventh feature (11), the condition changing means comprises means for changing, when the calculated blood oxygen saturation value is smaller than the predetermined third value, the predetermined first condition to the changed first condition that the at least one of the respective values based on the plurality of blood-pressure-relating values does not fall within the changed first range; and means for determining the changed first range based on a difference between the calculated blood oxygen saturation value and the predetermined third value.

(13) According to a thirteenth feature of the present invention that includes any one of the fifth to twelfth features (5) to (12), the blood-pressure-measurement starting means comprises periodically starting means for periodically starting a blood-pressure measurement of the measuring device at a predetermined period.

(14) According to a fourteenth feature of the present invention that includes the thirteenth feature (13), the blood-pressure monitoring apparatus further comprises period changing means for changing, when the blood-pressure value of the living subject measured by the measuring device is lower than a reference value, the predetermined period to a changed period shorter than the predetermined period so that the periodically starting means starts a blood-pressure measurement of the measuring device at the changed period. In this case, the measuring device can earlier measure a BP value of the living subject.

(15) According to a fifteenth feature of the present invention that includes any one of the fifth to fourteenth features (5) to (14), the blood-pressure-relating-value calculating means comprises a pulse-wave-propagation-relating-information obtaining device which iteratively obtains a piece of pulse-wave-propagation-relating information relating to propagation of a pulse wave through an arterial vessel of the living subject; relationship determining means for determining a relationship between pulse-wave-propagation-relating information and blood pressure, based on at least one blood-pressure value of the living subject measured by the measuring device and at least one piece of pulse-wave-propagation-relating information obtained by the pulse-wave-propagation-relating-information obtaining device; and estimating means for iteratively estimating, as the calculated blood-pressure-relating value, a blood-pressure value of the living subject, based on each piece of pulse-wave-propagation-relating information of a plurality of pieces of pulse-wave-propagation-relating information obtained by the pulse-wave-propagation-relating-information obtaining device, according to the determined relationship between pulse-wave-propagation-relating information and blood pressure.

(16) According to a sixteenth feature of the present invention that includes the fifteenth feature (15), the pulse-wave-propagation-relating-information obtaining device comprises at least one of pulse-wave-propagation-time calculating means for iteratively calculating a pulse-wave propagation time which is needed for each of a plurality of heartbeat-synchronous pulses of the pulse wave to propagate between two portions of the arterial vessel of the living subject, and pulse-wave-propagation-velocity calculating means for iteratively calculating a pulse-wave propagation velocity at which each of a plurality of heartbeat-synchronous pulses of the pulse wave propagates between two portions of the arterial vessel of the living subject.

(17) According to a seventeenth feature of the present invention that includes any one of the fifth to sixteenth features (5) to (16), the blood-pressure-relating-value calculating means comprises at least one of pulse-period calculating means for iteratively calculating, as the calculated blood-pressure-relating value, a pulse period equal to a time interval between each pair of successive heartbeat-synchronous pulses of a pulse wave obtained from the living subject, and pulse-wave-area-relating-value calculating means for iteratively calculating, as the calculated blood-pressure-relating value, a pulse-wave-area-relating value relating to an area of each of a plurality of heartbeat-synchronous pulses of a pulse wave obtained from the living subject.

(18) According to an eighteenth feature of the present invention that includes any one of the fifth to seventeenth features (5) to (17), the blood-pressure-relating-value calculating means comprises at least one of an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a second body portion of the living subject, and which emits a light toward the second body portion and obtains a photoelectric pulse wave including a plurality of heartbeat-synchronous pulses, from the light received from the second body portion.

(19) According to a nineteenth feature of the present invention that includes any one of the fifth to seventeenth features (5) to (18), the starting means comprises means for starting, when the calculated blood-pressure-relating value satisfies the predetermined first condition, the blood-pressure measurement of the measuring device.

(20) According to a twentieth feature of the present invention that includes any one of the fifth to seventeenth features (5) to (18), the starting means comprises means for calculating, as the value based on the calculated blood-pressure-relating value, a change value relating to a change of a first calculated blood-pressure-relating value calculated by the blood-pressure-relating-value calculating means from a second blood-pressure-relating value calculated prior to the first calculated blood-pressure-relating value by the blood-pressure-relating-value calculating means; and means for starting, when the calculated change value satisfies the predetermined first condition, the blood-pressure measurement of the measuring device.

(21) According to a twenty-first feature of the present invention that includes any one of the fifth to twentieth features (5) to (20), the blood-pressure monitoring apparatus further comprises an informing device which informs, when the value based on the calculated blood-pressure-relating value satisfies the predetermined first condition, a user of an occurrence of an abnormality to the living subject.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which:

FIG. 10 is a flow chart representing another control program according to which the control device of the apparatus of FIG. 1 is operated for determining an estimated BP value EBP of the living subject;

FIG. 11 is a graph representing a relationship between blood oxygen saturation $SaO_2$ and reference range, the reference range being used for finding an abnormal estimated BP value EBP; and FIG. 12 is a BP-measurement-start judging routine carried out at Step SB11 of FIG. 11.

DETAILED DESCRIPTION OF THE PREFERRED EMBODIMENTS

Figure 1:
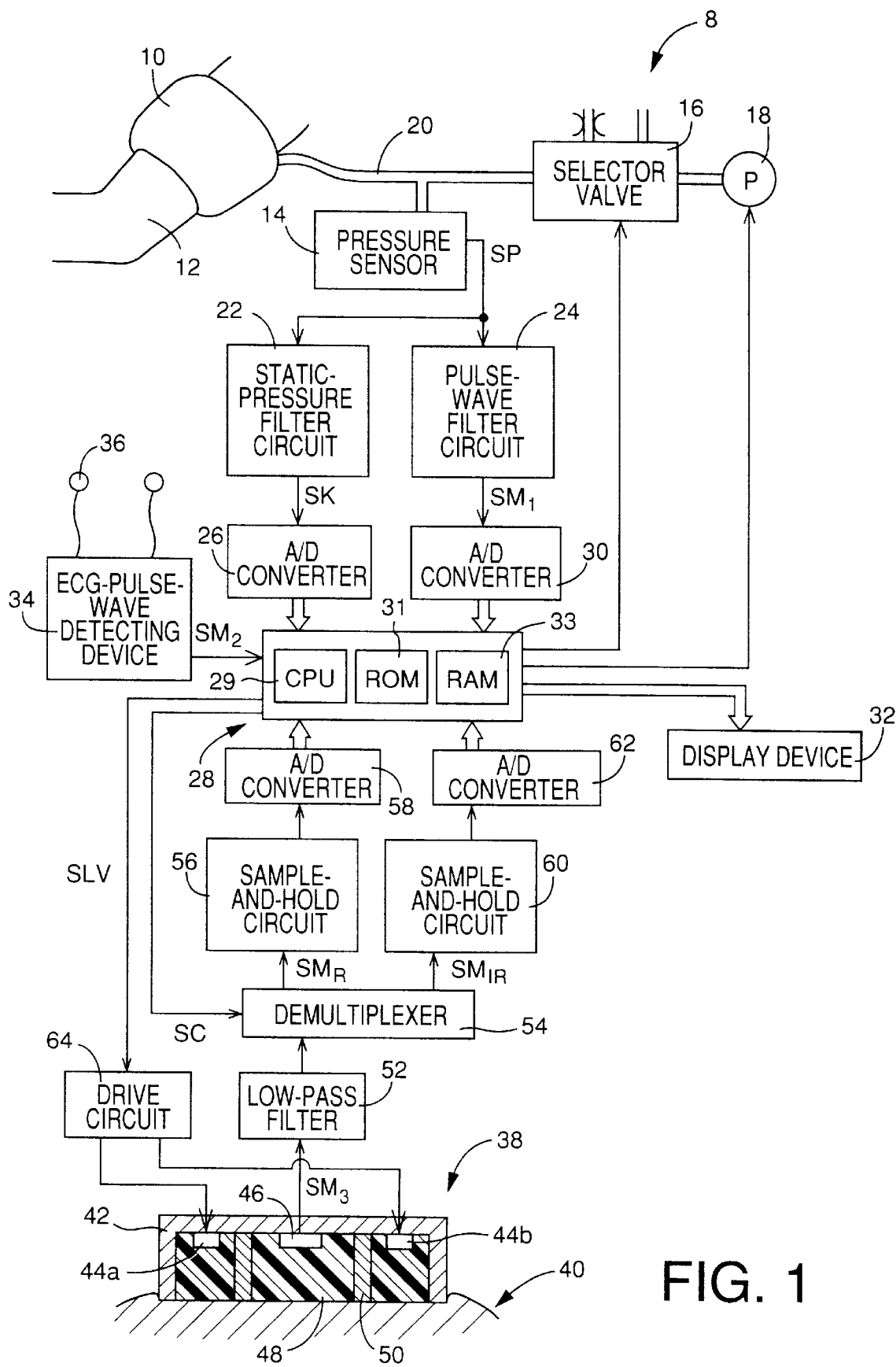
FIG. 1 is a diagrammatic view of a blood-pressure ("BP") monitoring apparatus embodying the present invention.

Referring to FIG. 1, there will be described a blood-pressure ("BP") monitoring apparatus 8 embodying the present invention.

In FIG. 1, the BP monitoring apparatus 8 includes an inflatable cuff 10 which has a belt-like cloth bag and a rubber bag accommodated in the cloth bag and which is adapted to be wrapped around, e.g., a right upper arm 12 of a patient as a living subject, and a pressure sensor 14, a selector valve 16 and an air pump 18 each of which is connected to the cuff 10 via piping 20. The selector valve 16 is selectively placed in an inflation position in which the selector valve 16 permits a pressurized air to be supplied from the air pump 18 to the cuff 10, a slow-deflation position in which the selector valve 16 permits the pressurized air to be slowly discharged from the cuff 10, and a quick-deflation position in which the selector valve 16 permits the pressurized air to be quickly discharged from the cuff 10.

The pressure sensor 14 detects an air pressure in the inflatable cuff 10, and supplies a pressure signal SP representative of the detected pressure to each of a static-pressure filter circuit 22 and a pulse-wave filter circuit 24. The static-pressure filter circuit 22 includes a low-pass filter and extracts, from the pressure signal SP, a static component contained in the signal SP, i.e., cuff-pressure signal SK representative of the static cuff pressure. The cuff-pressure signal SK is supplied to an electronic control device 28 via an analog-to-digital ("A/D") converter 26. The pulse-wave filter circuit 24 includes a band-pass filter and extracts, from the pressure signal SP, an oscillatory component having predetermined frequencies, i.e., cuff-pulse-wave signal $SM_1$. The cuff-pulse-wave signal $SM_1$ is supplied to the control device 28 via an A/D converter 30. The cuff-pulse-wave signal $SM_1$ is representative of the cuff pulse wave, i.e., oscillatory pressure wave which is produced from a brachial artery (not shown) of the patient in synchronism with the heartbeat of the patient and is propagated to the inflatable cuff 10.

The control device 28 is provided by a so-called microcomputer including a central processing unit ("CPU") 29, a read only memory ("ROM") 31, a random access memory ("RAM") 33, and an input-and-output ("I/O") port (not shown). The CPU 29 processes signals according, to control programs pre-stored in the ROM 31 by utilizing a temporary-storage function of the RAM 33, and supplies drive signals to the selector valve 16 and the air pump 18 through the I/O port.

The BP monitoring apparatus 8 further includes an electrocardiographic (ECG) pulse wave detecting device 34 which continuously detects an ECG pulse wave representative of the action potential of cardiac muscle of the patient, through a plurality of electrodes 36 being put on predetermined body portions of the patient, and supplies an ECG-pulse-wave signal $SM_2$ representative of the detected ECG pulse wave, to the control device 28. The ECG-pulse-wave detecting device 34 is used for detecting a Q-wave or an R-wave of each heartbeat-synchronous pulse of the ECG pulse wave that corresponds to a time point when the outputting of blood from the heart of the patient toward the aorta is started. Thus, the ECG-pulse-wave detecting device 34 functions as a first pulse-wave detecting device.

The BP monitoring apparatus 8 further includes a photoelectric-pulse-wave detecting probe 38 (hereinafter, referred to as the "probe" 38) which is employed as part of a pulse oximeter. The probe 38 functions as a second pulse-wave detecting device, or a peripheral-pulse-wave detecting device for detecting a peripheral pulse wave propagated to a peripheral artery including capillaries. The probe 38 is set on a skin or a body surface 40 of the patient, e.g., an end portion of a finger of a left hand of the patient with the help of a band (not shown), such that the probe 38 is held in close contact with the body surface 40. The probe 38 is worn on the hand of one arm different from the other arm around which the cuff 10 is wrapped.

The probe 38 includes a container-like housing 42 which opens in a certain direction, a first and a second group of light emitting elements 44a, 44b, such as LEDs (light emitting diodes), which are disposed on an outer peripheral portion of an inner bottom surface of the housing 42 (hereinafter, referred to as the light emitting elements 44 in the case where the first and second groups of light emitting elements 44a, 44b need not be discriminated from each other), a light receiving element 46, such as a photodiode or a phototransister, which is disposed on a central portion of the inner bottom surface of the housing 42, a transparent resin 48 which is integrally disposed in the housing 42 to cover the light emitting elements 44 and the light receiving element 46, and an annular shading member 50 which is disposed between the light emitting elements 44 and the light receiving element 46, for preventing the light receiving element 46 from receiving the lights emitted toward the body surface 40 by the light emitting elements 44 and directly reflected from the body surface 40.

The first group of light emitting elements 44a emit a first light having a first wavelength $\lambda_1$ whose absorbance changes depending on a blood oxygen saturation value of the patient. The first elements 44a emit, e.g., a red light having about 660 nm wavelength. The second group of light emitting elements 44b emit a second light having a second wavelength $\lambda_2$ whose absorbance does not change depending on the blood oxygen saturation value of the patient. The second elements 44b emit, e.g., an infrared light having about 800 nm wavelength. The first and second light emitting elements 44a, 44b alternately emit the red and infrared lights, respectively, at a predetermined frequency, e.g., a relatively high frequency of several hundred Hz to several thousand Hz. The lights emitted toward the body surface 40 by the light emitting elements 44 are reflected from a body tissue of the patient where a dense capillaries occur, and the reflected lights are received by the common light receiving element 46. In place of the 660 nm and 800 nm lights, the first and second light emitting elements 44a, 44b may employ various pairs of lights each pair of which have different wavelengths, so long as one light of each pair exhibits significantly different absorption factors with respect to oxygenated hemoglobin and reduced hemoglobin, respectively, and the other light exhibits substantially same absorption factors with respect to the two sorts of hemoglobin, i.e., has a wavelength which is reflected by each of the two sorts of hemoglobin.

Figure 2:
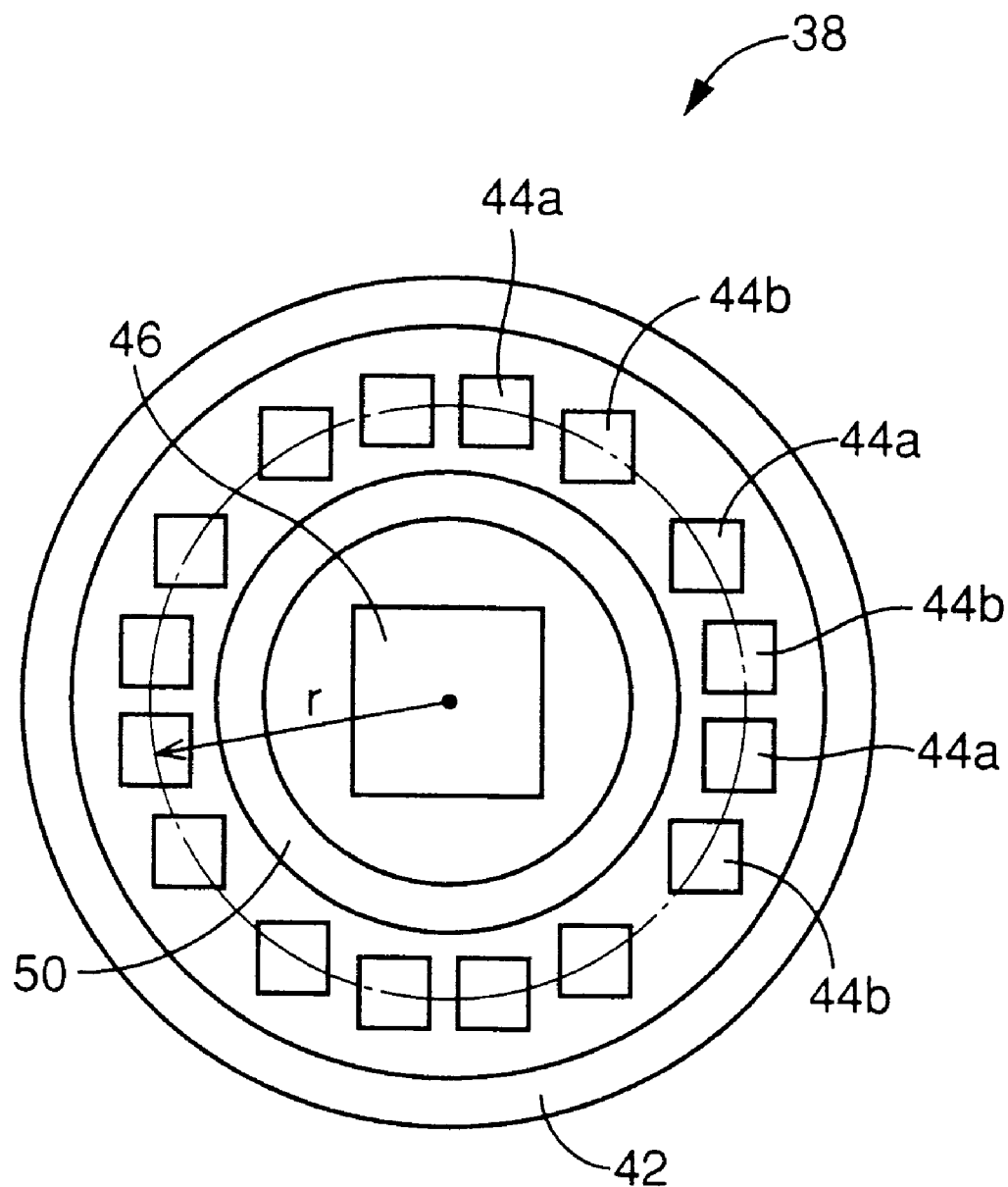
FIG. 2 is a bottom view of a reflection-type photoelectric-pulse-wave detecting probe of the apparatus of FIG. 1.

FIG. 2 shows a bottom surface of the probe 38 or the housing 42 that is opposed to the body surface 40 of the patient. The light receiving element 46 is located on the central portion of the housing 42, and the annular shading member 50 is fixed to the housing 42 such that the shading member 50 is concentric with the circular housing 42. The first light emitting elements 44a and the second light emitting elements 44a are alternately arranged along a circle, indicated by a one-dot chain line, which is located outside the shading member 50, has a radius, r, and is concentric with the shading member 50 and the housing 42.

The light receiving element 46 outputs, through a low-pass filter 52, a photoelectric-pulse-wave signal $SM_3$ representative of an amount of the first or second light received from the body tissue of the patient. The light receiving element 46 is connected to the low-pass filter 52 via an amplifier or the like. The low-pass filter 52 removes, from the photoelectric-pulse-wave signal $SM_3$ input thereto, noise having frequencies higher than that of a pulse wave, and outputs the noise-free signal $SM_3$, to a demultiplexer 54. The photoelectric-pulse-wave signal $SM_3$ is representative of a photoelectric pulse wave which is produced in synchronism with the pulse of the patient.

The demultiplexer 54 is switched according to signals supplied thereto from the control device 28 in synchronism with the alternate light emissions of the first and second light emitting elements 44a, 44b. Thus, the demultiplexer 54 separates the photoelectric-pulse-wave ("PPW") signal $SM_3$ into two PPW signals which correspond to the first and second lights, respectively. More specifically described, the demultiplexer 54 successively supplies, to the I/O port (not shown) of the control device 28, a first PPW signal $SM_R$ representative of the red light having the first wavelength $\lambda_1$ through a first sample-and-hold circuit 56 and an A/D converter 58, and a second PPW signal $SM_{IR}$ representative of the infrared light having the second wavelength $\lambda_2$ through a second sample-and-hold circuit 60 and an A/D converter 62. The first and second sample-and-hold circuits 56, 60 hold the first and second PPW signals $SM_R$, $SM_{IR}$ input thereto, respectively, and do not output those current signals to the A/D converters 58, 62, before the prior signals $SM_R$, $SM_{IR}$ are completely converted by the A/D converters 58, 62, respectively.

In the control device 28, the CPU 29 carries out a measuring operation according to control programs pre-stored in the ROM 31 by utilizing the temporary-storage function of the RAM 33. More specifically described, the CPU 29 generates a light emit signal SLV to a drive circuit 64 so that the first and second light emitting elements 44a, 44b alternately emit the red and infrared lights at a predetermined frequency, respectively, such that each light emission lasts for a predetermined duration. In synchronism with the alternate light emissions of the first and second light emitting elements 44a, 44b, the CPU 29 generates a switch signal SC to the demultiplexer 54 to switch the demultiplexer 54 between its first and second positions. Thus, the PPW signal $SM_3$ is separated by the demultiplexer 54 such that the first PPW signal $SM_R$ is supplied to the first sample-and-hold circuit 56 while the second PPW signal $SM_{IR}$ is supplied to the second sample-and-hold circuit 60.

Figure 3:
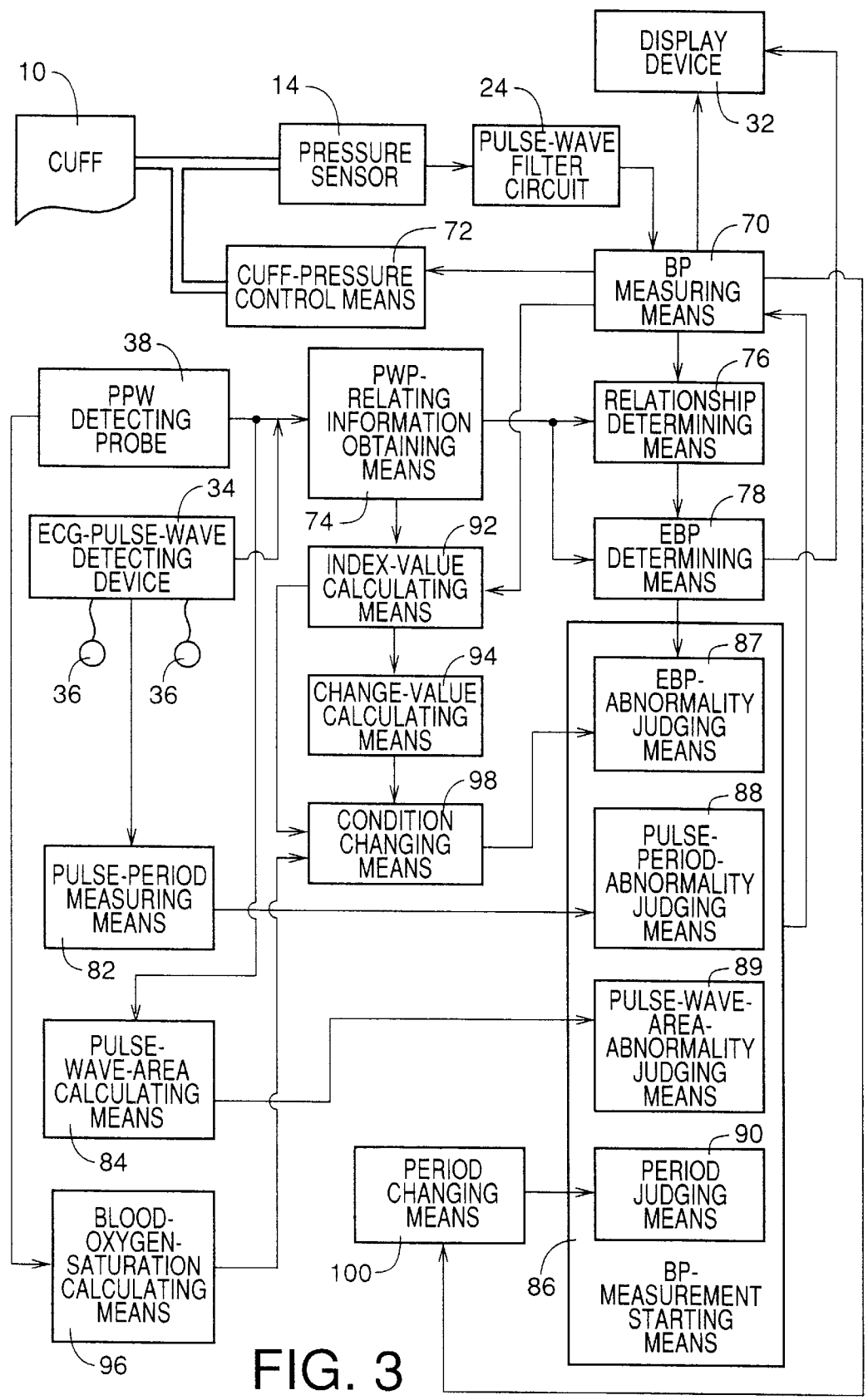
FIG. 3 is a block diagram for illustrating essential functions of an electronic control device of the apparatus of FIG. 1.

FIG. 3 illustrates essential functions of the control device 28 of the present BP monitoring apparatus 8. In the figure, a BP measuring means or circuit 70 measures a systolic, a mean, and a diastolic BP value $BP_{SYS}$, $BP_{MEAN}$, $BP_{DIA}$ of the patient, according to a well known oscillometric method, based on the variation of respective amplitudes of heartbeat-synchronous pulses of the pulse wave represented by the cuff-pulse-wave signal $SM_1$ obtained while the cuff pressure which is quickly increased by a cuff-pressure control means or circuit 72 to a target pressure value PCM (e.g., 180 mmHg), is slowly decreased at the rate of about 3 mmHg/sec.

Figure 4:
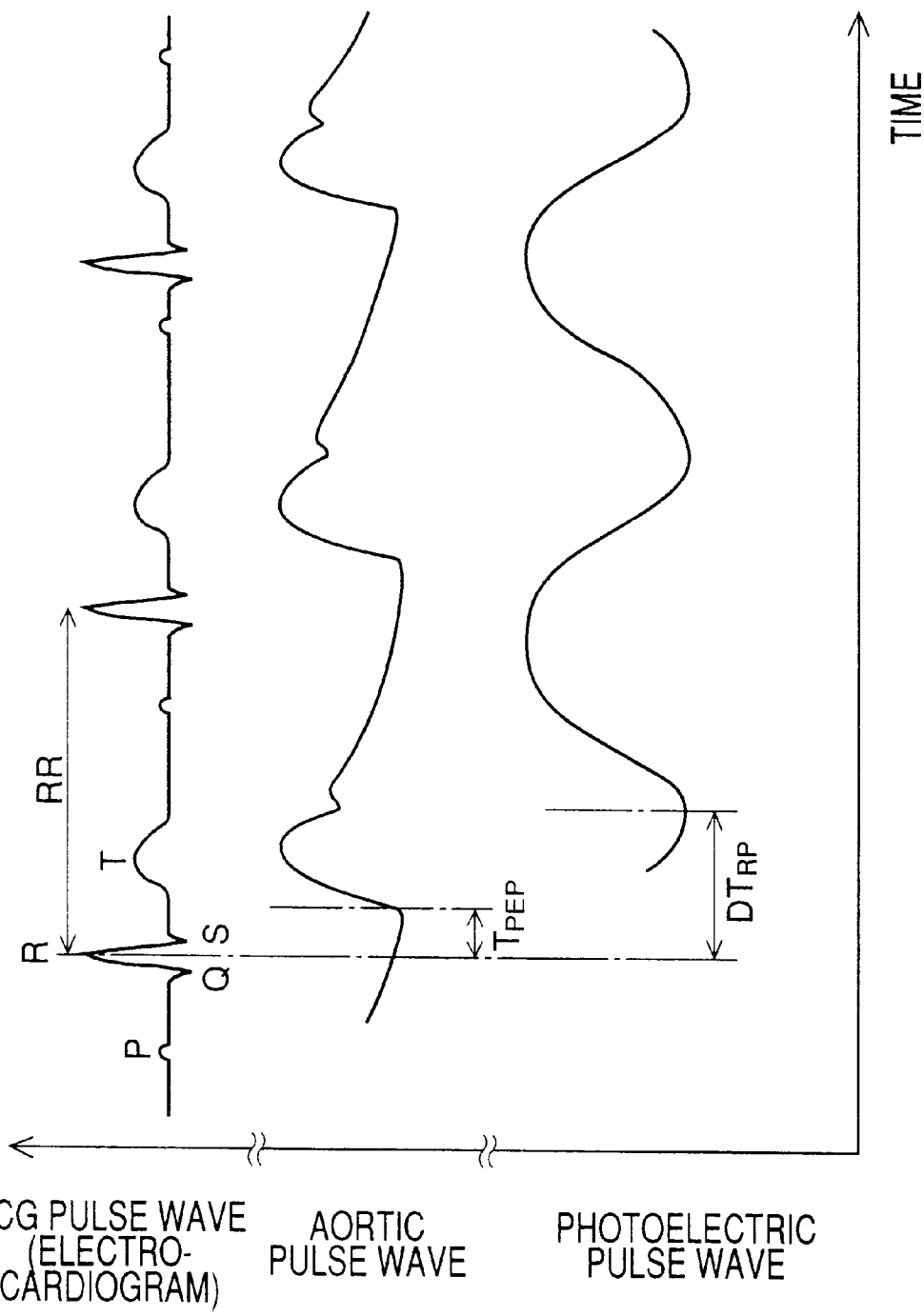
FIG. 4 is a view for illustrating a pulse-wave propagation time $DT_{RP}$ obtained by an operation of the control device of the apparatus of FIG. 1.

A pulse wave propagation ("PWP") relating information obtaining means or circuit 74 includes a time-difference calculating means or circuit which iteratively calculates, as a PWP time $DT_{RP}$, a time difference between a predetermined point (e.g., R-wave) on the waveform of each of periodic pulses of the ECG pulse wave that are successively detected by the ECG-pulse-wave detecting device 34 and a predetermined point (e.g., rising point, i.e., minimum point) on the waveform of a corresponding one of periodic pulses of the photoelectric pulse wave ("PPW") detected by the probe 38, as illustrated in FIG. 4. The PPW-relating-information obtaining means 74 iteratively calculates a PWP velocity $V_M$ (m/sec) of a pulse wave propagated through an artery of the patient, based on the calculated PPW time $DT_{RP}$, according to the following expression (1) pre-stored in the ROM 31:

$$V_M = L/(DT_{RP} - T_{PEP}) \tag{1}$$

where L (m) is a length of the artery as measured from the left ventricle to the position where the probe 38 is set, via the aorta; and $T_{PEP}$ (sec) is a pre-ejection period between the R-wave of the waveform of each pulse of the ECG pulse wave and the minimum point of the waveform of a corresponding pulse of an aortic pulse wave.

The values L, $T_{PEP}$ are constants, and are experimentally obtained in advance.

A relationship determining means or circuit 76 determines two coefficients α, β in the following second or third expression (2) or (3), based on two systolic BP values $BP_{SYS}$ measured by the BP measuring means 70, and two PWP time values $DT_{RP}$ or two PWP velocity values $V_M$ calculated by the PPW-relating-information obtaining means 74. Each value $DT_{RP}$, $V_M$ may be an average of several values $DT_{RP}$, $V_M$ which are obtained immediately before each BP measurement. The above two expressions (2), (3) generally define a relationship between PWP time value $DT_{RP}$ and estimated BP value EBP, and a relationship between PWP velocity value $V_M$ and estimated BP value EBP, respectively. In place of the above-indicated relationship between estimated systolic BP value $EBP_{SYS}$ and either one of PWP time value $DT_{RP}$ and PWP velocity value $V_M$, a relationship between estimated mean or diastolic BP value $EBP_{MEAN}$, $EBP_{DIA}$ and either one of PWP time value $DT_{RP}$ and PWP velocity value $V_M$ may be employed. In short, a relationship between PWP-relating information and estimated BP value EBP may be determined depending upon which one of systolic, mean, and diastolic BP value is selected as estimated BP value EBP, i.e., monitored BP value.

$$EBP = \alpha(DT_{RP}) + \alpha \tag{2}$$

where α is a negative constant and β is a positive constant.

$$EBP = \alpha(V_M) + \beta \tag{3}$$

where α and β are positive constants.

An estimated-BP ("EBP") determining means or circuit 78 iteratively determines an estimated BP value EBP of the patient, based on either one of an actual PWP time value $DT_{RP}$ and an actual PWP velocity value $V_M$ iteratively calculated by the PWP-relating-information obtaining means 74, according to the relationship represented by the second or third expression (2) or (3).

Figure 5:
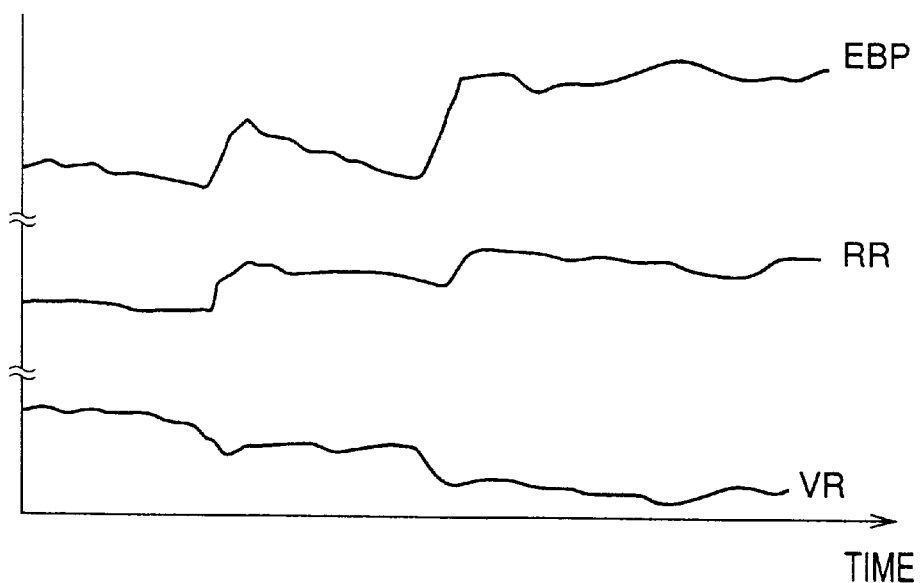
FIG. 5 is a view for illustrating respective trend graphs of estimated BP values EBP, pulse period values RR, and pulse-wave area values VR which are obtained by the apparatus of FIG. 1 and are concurrently displayed by a display device of the same.

The control device 28 controls a display device 32 to concurrently display a trend graph of the thus determined estimated BP values EBP, together with respective trend graphs of pulse period values RR and pulse-wave area values VR (which will be described below), along a common horizontal axis indicative of time, as shown in FIG. 5, so that those three trend graphs can be compared with one another by a medical person, such as a doctor or a nurse, who attend to the patient.

A pulse-period measuring means or circuit 82 iteratively measures a pulse period value RR by measuring or calculating a time difference between respective predetermined points (e.g., R-waves) of each pair of successive heartbeat-synchronous pulses of the ECG pulse wave detected by the ECG-pulse-wave detecting device 34.

Figure 6:
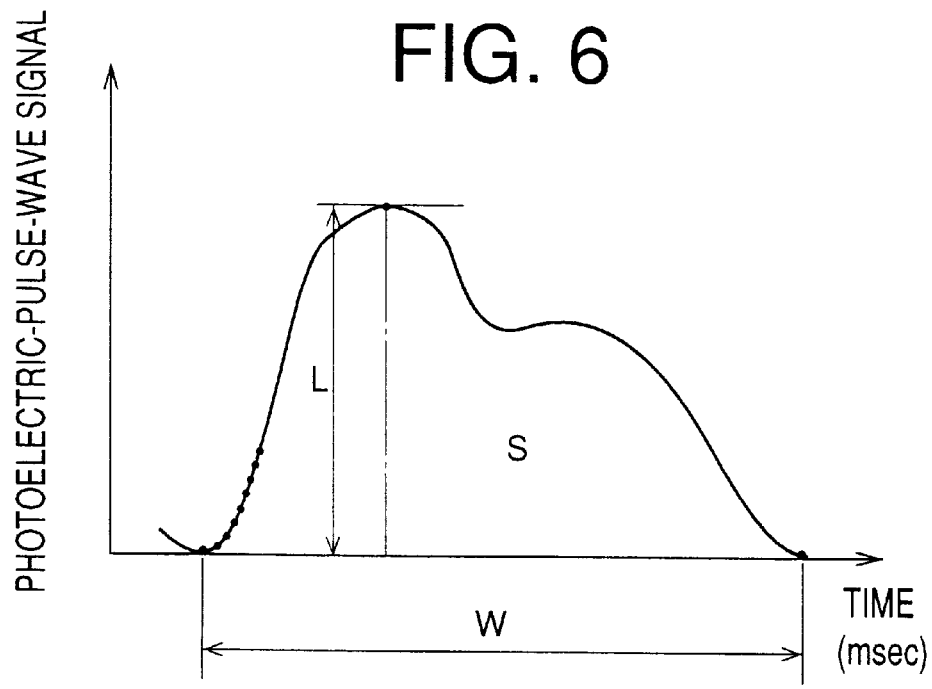
FIG. 6 is a view for explaining the manner in which a normalized pulse-wave area value VR is obtained.

A pulse-wave-area calculating means or circuit 84 calculates a pulse-wave area value VR by normalizing an area S defined or enveloped by the waveform of each heartbeat-synchronous pulse of the PPW detected by the probe 38, based on a period W and an amplitude L of the each pulse. More specifically described, as shown in FIG. 6, the waveform of each pulse of the PPW is defined by a series of data points indicative of respective magnitudes which are input at a predetermined short interval such as several milliseconds to several tens of milliseconds. The pulse-wave area S is obtained by integrating, over the period W of the each pulse, respective magnitudes of the data points of the each pulse, and then the normalized pulse-wave area value VR is obtained according to the following expression: VR=S/(W× L). The normalized pulse-wave area value VR is a dimensionless value indicative of the ratio of the pulse-wave area S to a rectangular area defined by the period W and the amplitude L of the each pulse. For this parameter, the symbol "%MAP" may be used in place of the symbol "VR".

A BP-measurement starting means or circuit 86 starts a BP-measurement of the BP measuring means 70, when the absolute value of at least one value based on at least one estimated BP value EBP is not smaller than a first reference value and simultaneously at least one of the absolute value of at least one value based on at least one measured pulse period value RR and the absolute value of at least one value based on at least one calculated pulse-wave area value VR is not smaller than a corresponding one of a second and a third reference value, or periodically at a predetermined period $T_{BP}$, e.g., 20 minutes. A value based on each estimated BP value EBP may be the each value EBP itself, or a change value that is an amount of change of the each value EBP from a "control" value EBP determined at the time of the last BP measuring operation, or the ratio of the amount of change to the "control" value EBP. Similarly, a value based on each measured pulse period value RR may be the each value RR itself, or a change value that is an amount of change of the each value RR from a "control" value RR measured at the time of the last BP measuring operation, or the ratio of the amount of change to the "control" value RR, and a value based on each calculated pulse-wave area value VR may be the each value VR itself, or a change value that is an amount of change of the each value VR from a "control" value VR calculated at the time of the last BP measuring operation, or the ratio of the amount of change to the "control" value VR.

More specifically described, the BP-measurement starting means 86 includes an EBP-abnormality judging means for judging that each estimated BP value EBP determined by the EBP determining means 78 is abnormal when at least one value based on at least one value EBP including the each value EBP does not fall within a first reference range; an RR-abnormality judging means for judging that each pulse period value RR measured by the pulse-period measuring device 82 is abnormal when at least one value based on at least one value RR including the each value RR does not fall within a second reference range; a VR-abnormality judging means for judging that each pulse-wave area value VR calculated by the pulse-wave area calculating means 84 is abnormal when at least one value based on at least one value VR including the each value VR does not fall within a third reference range; and a period judging means or circuit 90 for judging whether time has passed by the predetermined period $T_{BP}$. For example, when the EBP-abnormality judging means 87 judges that an estimated BP value EBP is abnormal and simultaneously at least one of the RR-abnormality judging means 88 and the VR-abnormality judging means 89 judges that a corresponding one of a pulse period value RR and a pulse-wave area value VR is abnormal, or when the period judging means 90 judges that time has passed by the predetermined period $T_{BP}$, the BP-measurement starting means 86 may start a BP measurement of the BP measuring means 70.

An index-value calculating means or circuit 92 calculates, based on the BP values measured in the last or current BP measuring operation of the BP measuring means 70, an index value $I_a$ indicative of a hardness of an arterial vessel of the patient. More specifically described, the index-value calculating means 92 calculates a pulse pressure $P_M$ by subtracting the measured diastolic BP value $BP_{DIA}$ from the measured systolic BP value $BP_{SYS}$, and calculates an index value $I_a$ by dividing the pulse pressure $P_M$ by the measured mean BP value $BP_{MEAN}$ (i.e. $I_a=P_M/BP_{MEAN}$). Meanwhile, it is known that as the arterial vessel becomes harder, the PWP velocity value $V_M$ becomes greater. Therefore, the index-value calculating means 92 may calculate an index value $I_a$ by dividing the PWP velocity value $V_M$, or the inverse of the PWP time value $DT_{RP}$, by a BP value BP measured by the BP measuring means 70 (e.g., measured systolic, mean, or diastolic BP value $BP_{SYS}$, $BP_{MEAN}$, $BP_{DIA}$) (i.e. $I_a=V_M/BP$, or $I_a=(1/DT_{RP})/BP$).

A change-value calculating means or circuit 94 calculates, as a value relating to a change of a calculated index value $I_a$, a change value $\Delta I_a$ that is an amount of change of the "current" index value $I_a$ calculated at the time of the last or current BP measuring operation, from a "control" value $I_a$ calculated at the time of the BP measuring operation prior to the current BP measuring operation, or the ratio of the amount of change to the "control" value $I_a$ Alternatively, the change-value calculating means 94 may calculate a change value $\Delta I_a$ that is an amount of change of the "current" index value $I_a$ from a moving average of a predetermined number (e.g., from 3 to 5) of index values $I_a$ calculated at respective times of a corresponding number of late BP measuring operations including the last or current BP measuring operation.

A blood-oxygen-saturation calculating means or circuit 96 includes a frequency-analysis means or circuit which applies a frequency analysis using the method of fast Fourier transform, to each of a plurality of predetermined intervals of each of the two PPW signals $SM_R$ $SM_{IR}$ supplied from the demultiplexer 54, and determines a direct-current component $DC_R$ and an alternating-current component $AC_R$ of each of the intervals of the first PPW signal $SM_R$ and a direct-current component $DC_{IR}$ and an alternating-current component $AC_{IR}$ of each of the intervals of the second PPW signal $SM_{IR}$; and a ratio calculating means or circuit which calculates the ratio (i.e., $AC_R/DC_R$) of the alternating-current component $AC_R$ to the direct-current component $DC_R$ of each of the intervals of the PPW signal $SM_R$ and the ratio (i.e., $AC_{IR}/DC_{IR}$) of the alternating-current component $AC_{IR}$ to the direct-current component $DC_{IR}$ of each of the intervals of the PPW signal $SM_{IR}$. The blood-oxygen-saturation calculating means 96 calculates a blood oxygen saturation value $SaO_2$ of the patient based on the ratio R (i.e., $(AC_R/DC_R)/(AC_{IR}/DC_{IR})$ of the first ratio $AC_R/DC_R$ to the second ratio $AC_{IR}/DC_{IR}$ according to the following expression (4):

$$SaO_2 = A \times R + B \qquad (4)$$

where A is a negative constant indicative of the slope of a straight line represented by the expression (4); and β is a constant indicative of the intercept of the straight line.

Each interval to which the frequency analysis is applied by the frequency-analysis means is predetermined at a multiple of a full respiration period $T_{RE}$, or half the period $T_{RE}$, of the patient (e.g., a multiple of a time equal to four or two times each measured pulse period value RR of the patient), in order to remove respiratory changes from the PPW signals $SM_R$, $SM_{IR}$.

A condition changing means or circuit 98 changes, when the index value $I_a$ calculated by the index-value calculating means 92 does not fall within a fourth reference range, when the change value $\Delta I_a$ calculated by the change-value calculating means 94 does not fall within a fifth reference range, or when the blood oxygen saturation value $SaO_2$ calculated by the blood-oxygen-saturation calculating means 96 is smaller than a reference value, the first, second, and/or third reference range to a changed first, a changed second, and/or a changed third reference range out of which at least one value based on at least one estimated BP value EBP, at least one value based on at least one measured pulse period value RR, and/or at least one value based on at least one calculated pulse-wave area value VR can go, respectively, than can go out of the initial first, second, and/or third reference range, respectively. Each of the changed first, second, and/or third reference range may be a predetermined range, or may be changed stepwise or continuously based on the difference between the calculated index value $I_a$ and the upper or lower limit value of the fourth reference range, the difference between the calculated change value $\Delta I_a$ and the upper or lower limit value of the fifth reference range, and/or the difference between the calculated blood oxygen saturation value $_2$ and the reference value.

However, each of the initial first, second, and third reference ranges may be replaced with only one of the upper and lower limit values of the each range. For example, in the case where the first to third reference ranges are replaced with only the respective lower limit values thereof, the condition changing means 98 changes the first, second, and/or third lower limit values to changed first, second, and/or third lower limit values greater than the initial first, second, and/or third lower limit values, respectively; and in the case where the first, second, and third reference ranges are replaced with only the respective upper limit values thereof, the condition changing means 98 changes the first, second, and/or third upper limit values to changed first, second, and/or third upper limit values smaller than the initial first, second, and/or third lower limit values, respectively.

When the index value $I_a$ does not fall within the fourth reference range, it can be speculated that the flexibility or elasticity of the arterial vessels of the patient may have been lost because of arteriosclerosis or temporary constriction of the arterial vessels and accordingly the BP of the patient cannot be easily controlled, or that the patient may have fallen in shock because of excessive expansion of the arterial vessels. Therefore, it can be judged that the patient needs quick treatments. When the change value $\Delta I_a$ does not fall within the fifth reference range, it can be speculated that the accuracy of the estimated BP values EBP may have decreased because the hardness of the arterial vessels has largely changed during the monitoring of BP of the patient. When the blood oxygen saturation value $SaO_2$ is smaller than the reference value, it can be speculated that the blood oxygen saturation $SaO_2$ measured from the peripheral body portion (e.g., finger) of the patient may have largely decreased because the arterial vessels have constricted and accordingly the amount of blood flowing through the peripheral body portion has decreased. More specifically described, when the BP of the patient becomes abnormal because the arterial vessels constrict, the blood oxygen saturation $SaO_2$ may decrease before the BP becomes abnormal. That is, when the blood oxygen saturation $SaO_2$ decreases, the BP may subsequently become abnormal.

A period changing means or circuit 100 changes, when a BP value (e.g., systolic BP value $BP_{SYS}$) measured by the BP measuring means 70 is smaller than a predetermined alarm value AL (e.g., 80 mmHg), the predetermined period $T_{BP}$ (e.g., 20 minutes) to a shorter period $T_{BP}'$ (e.g., 10 minutes).

Next, there will be described the operation of the control device 28 of the BP monitoring apparatus 8 by reference to the flow charts of FIGS. 7, 10, and 12. The flow chart of FIG. 7 represents the BP measuring routine; the flow chart of FIG. 10 represents the EBP determining routine; and the flow chart of FIG. 12 represents the BP-measurement-start judging routine.

Figure 7:
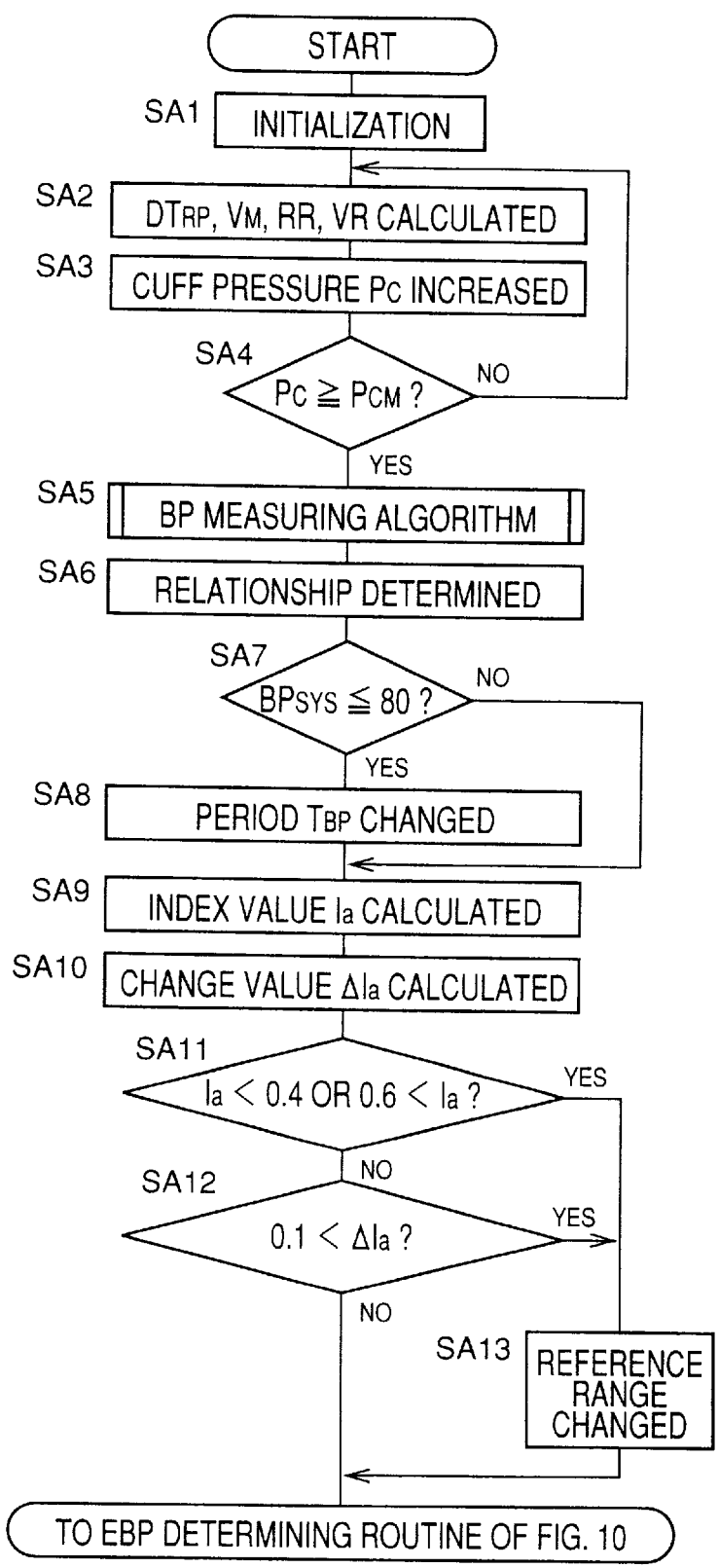
FIG. 7 is a flow chart representing a control program according to which the control device of the apparatus of FIG. 1 is operated for measuring, using an inflatable cuff, a BP value of a living subject.

The control of the CPU 29 begins with Step SA1 of the flow chart of FIG. 7, where flags, counters, and registers (not shown) are reset, that is, the initialization of the control device 28 is carried out. Step SA1 is followed by Step SA2 to calculate, as a PWP time value $DT_{RP}$, a time difference between a R-wave of the waveform of a heartbeat-synchronous pulse of the ECG pulse wave and a rising point of the waveform of a corresponding pulse of the PPW which are obtained immediately before the increasing of the cuff pressure, and additionally calculate a PWP velocity value $V_M$ (m/sec) based on the calculated PWP time value $DT_{RP}$ according to the expression (1). Step SA2 corresponds to the PWP-relating-information obtaining means 74. In addition, the CPU 29 calculates a pulse period value RR based on the time interval between two successive pulses of the ECG pulse wave, and calculates a normalized pulse-wave area value VR from the waveform of a pulse of the PPW. Thus, Step SA2 also corresponds to the pulse-period measuring means 82 and the pulse-wave-area calculating means 84.

The control of the CPU 29 goes to Steps SA3 and SA4 corresponding to the cuff-pressure control means 72. At Step SA3, the CPU 29 quickly increases the cuff pressure PC for a BP measurement of the BP measuring means 70, by switching the selector valve 16 to the inflation position and operating the air pump 18. Step SA3 is followed by Step SA4 to judge whether or not the cuff pressure PC is equal to or greater than a predetermined target pressure value PCM (e.g., 180 mmHg). If a negative judgement is made at Step SA4, the control of the CPU 29 goes back to Step SA2 so as to continue increasing the cuff pressure $P_C$.

If a positive judgement is made at Step SA4, the control of the CPU 29 goes to Step SA5 to carry out a BP measuring algorithm. More specifically described, the air pump 18 is stopped and the selector value 16 is switched to the slow-deflation position where the valve 16 permits the pressurized air to be slowly discharged from the cuff 10. A systolic BP value $BP_{SYS}$, a mean BP value $BP_{MEAN}$, and a diastolic BP value $BP_{DIA}$ are determined, according to a well known oscillometric BP determining algorithm, based on the variation of respective amplitudes of heartbeat-synchronous pulses of the pulse wave represented by the cuff-pulse-wave signal $SM_1$ obtained while the cuff pressure $P_C$ is slowly decreased at a predetermined rate of about 3 mmHg/sec, and a heart rate HR is determined based on the interval of two successive pulses of the pulse wave. The thus measured BP values and heart rate HR are displayed on the display device 32, and the selector valve 16 is switched to the quick-deflation position where the valve 16 permits the pressurized air to be quickly discharged from the cuff 10. Step SA5 corresponds to the BP measuring means 70.

Step SA5 is followed by Step SA6 to determine a relationship between PWP-relating information and estimated BP value EBP based on two BP values measured at Step SA5 in two control cycles each according to the flow chart of FIG. 7, and two PWP time values $DT_{RP}$ or two PWP velocity values $V_M$ calculated at Step SA2 in the two control cycles. More specifically described, when the systolic, mean, and diastolic BP values $BP_{SYS}$, $BP_{MEAN}$, $BP_{DIA}$ are measured at Step SA5, then at Step SA6 a relationship between estimated systolic, mean, or diastolic BP value $EBP_{SYS}$, $EBP_{MEAN}$, $EBP_{DIA}$ and one of PWP time value $DT_{RP}$ and PWP velocity value $V_M$, represented by the expression (2) or (3), is determined based on the two systolic, mean, or diastolic BP values $BP_{SYS}$, $BP_{MEAN}$, $BP_{DIA}$ measured at Step SA5 in the last two control cycles including the last or current control cycle, and the two PWP time or velocity values $DT_{RP}$, $V_M$ calculated at Step SA2 in the last two control cycles. Step SA6 corresponds to the relationship determining means 76. In addition, the CPU 29 determines an estimated BP value EBP of the patient based on the PWP time or velocity value $DT_{RP}$, $V_M$ determined at Step SA2, according to the thus determined relationship.

Step SA6 is followed by Step SA7 to judge whether the systolic BP value $BP_{SYS}$ measured at Step SA5 is smaller than a predetermined alarm value AL, e.g., 80 mmHg. If a negative judgment is made at Step SA7, the control of the CPU 29 skips Step SA8 and directly goes to Step SA9. On the other-hand, a positive judgment made at Step SA7 indicates that the BP of the patient should be carefully observed. Hence, subsequently the control goes to Step SA8 to change the predetermined period $T_{BP}$, e.g., 20 minutes, to a shorter period $T_{BP}$, e.g., 10 minutes. Step SA9 corresponds to the period changing means 100. Step SA8 is followed by Step SA9.

At Step SA9, the CPU 29 calculates an index value $I_a$ indicative of a hardness of a blood vessel of the patient, based on the systolic, mean, and diastolic BP values $BP_{SYS}$, $BP_{MEAN}$, $BP_{DIA}$ measured at Step SA5. The CPU 29 calculates a pulse pressure $P_M$ by subtracting the measured diastolic BP value $BP_{DIA}$ from the measured systolic BP value $BP_{SYS}$, and calculates the index value $I_a$ by dividing the pulse pressure $P_M$ by the measured mean BP value $BP_{MEAN}$.

Step SA9 is followed by Step SA10 where the CPU 29 calculates, as the change value $\Delta I_a$ of the index value $I_a$, an amount of change of the "current" index value $I_a$ calculated in the last or current control cycle according to the flow chart of FIG. 7, i.e., at the time of the last or current BP measuring operation, from the "control" index value $I_a$ calculated in the preceding or prior control cycle according to the flow chart of FIG. 7, i.e., at the time of the prior BP measuring operation, that is, calculates the absolute value of the difference between the two index values $I_a$. Step SA10 corresponds to the change-value calculating means 94.

Figure 8:
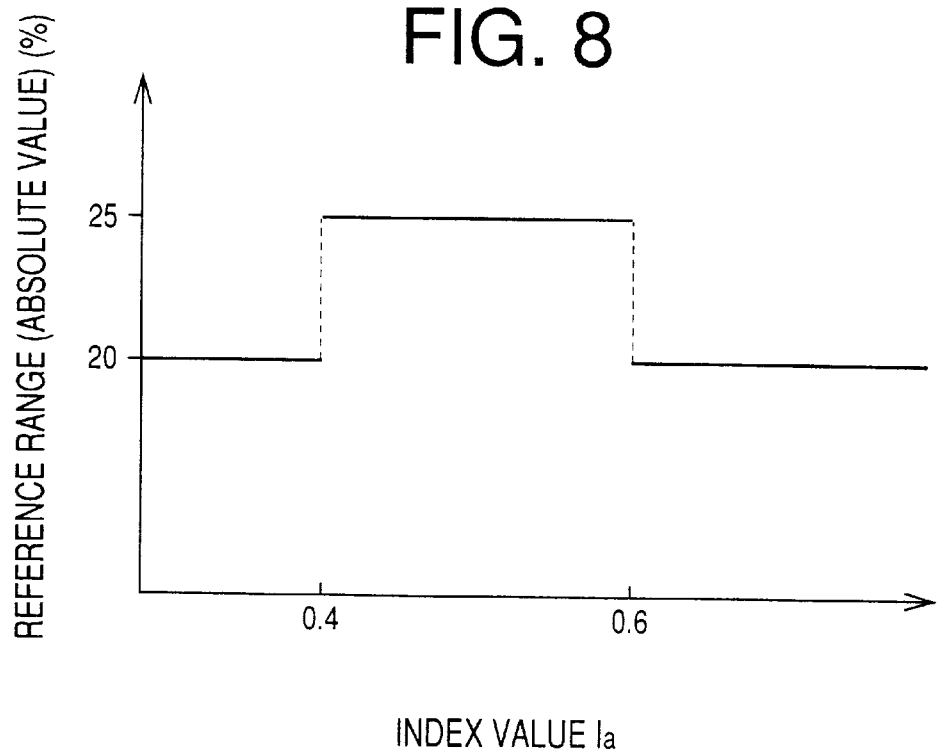
FIG. 8 is a graph representing a relationship between index value $I_a$ and reference range, the reference range being used for finding an abnormal estimated BP value EBP.

At Step SA11, the CPU 29 judges whether the index value $I_a$ calculated at Step SA9 in the current control cycle falls outside a predetermined normal index-value range, e.g., the range of from 0.4 to 0.6 shown in the graph of FIG. 8. The normal index-value range is experimentally determined in advance, on the assumption that the index value $I_a$ is calculated in the manner employed at Step SA9. The fact that the index value $I_a$ is smaller than the lower limit value, 0.4, indicates that the blood vessel of the patient is too soft and may have excessively largely expanded, and the fact that the index value $I_a$ is greater than the upper limit value, 0.6, indicates that the blood vessel of the patient is too hard and may have lost its flexibility or elasticity.

Figure 9:
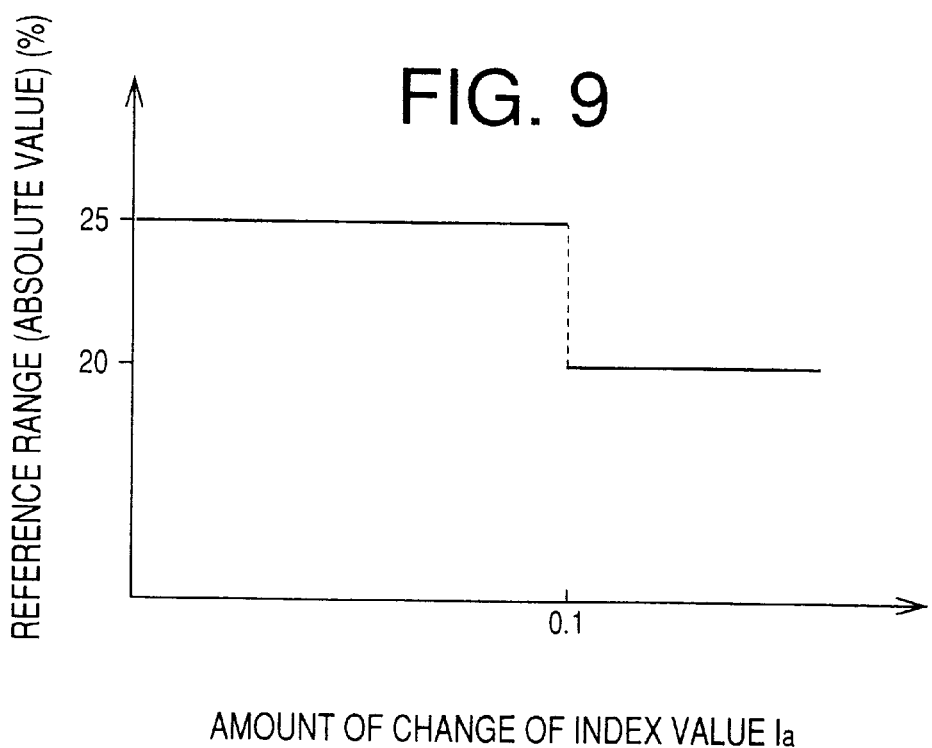
FIG. 9 is a graph representing a relationship between amount of change of index value $I_a$ and reference range, the reference range being used for finding an abnormal estimated BP value EBP.

If a negative judgment is made at Step SA11, the control of the CPU 29 goes to Step SA12 to judge whether the change value $\Delta I_a$ (i.e., the absolute value of the amount of change of the index value $I_a$) calculated at Step SA10 is greater than a predetermined reference value, e.g., 0.1 as shown in the graph of FIG. 9. This reference value is experimentally determined in advance, as a threshold or criterion value which indicates that assuming that the change value $\Delta I_a$ is calculated in the manner employed at Step SA10, the hardness of the blood vessel of the patient has significantly largely changed and accordingly the accuracy or reliability of the estimated BP value EBP determined at Step SA6 has been lost. Since the calculated change value $\Delta I_a$ is an absolute value, the predetermined reference value (e.g., 0.1) defines, in fact, a predetermined reference range (e.g., the range of from −0.1 to +0.1).

If a negative judgment is made at Step SA12, the CPU 29 terminates the BP measuring routine of FIG. 7 and proceeds with the EBP determining routine of FIG. 10. On the other hand, if a positive judgment is made at Step SA11 or Step SA12, the control of the CPU 29 goes to Step SA13 corresponding to the condition changing means 98, and then terminates the BP measuring routine of FIG. 7. At Step SA13, the CPU 29 changes a predetermined reference range employed at Step SB11 of FIG. 10 described later, to a changed reference range as shown in the graphs of FIGS. 8 and 9. At SB11, the CPU 29 judges that the "current" estimated BP value EBP determined at Step SB10 in the current control cycle is abnormal, when the absolute value of the ratio of the amount of change of the "current" estimated BP value EBP from the "control" estimated BP value EBP determined at Step SA6 at the time of the last BP measuring operation, to the "control" estimated BP value EBP, is greater than a predetermined reference value, e.g., 25%, after the absolute value of the ratio determined for each of not less than nineteen prior values EBP has been found as being greater than the reference value. Since the absolute value of the ratio determined for each estimated BP value EBP is compared with the reference value (e.g., 25%), the reference value defines, in fact, a predetermined reference range (e.g., the range of from −25% to +25%). If the index value $I_a$ calculated at Step SA9 does not fall within the normal index-value range of 0.4 to 0.6, or if the change value $\Delta I_a$ calculated at Step SA10 is greater than 0.1, the CPU 29 changes the predetermined reference range of, e.g., −25% to +25%, to a narrower range of, e.g., −20% to +20%.

After the BP measuring routine of FIG. 7, the control of the CPU 29 goes to the EBP determining routine of FIG. 10. First, at Step SB1, the CPU 29 judges whether an R-wave of the waveform of a heartbeat-synchronous pulse of the ECG pulse wave and a rising point of the waveform of a corresponding pulse of the photoelectric pulse wave ("PPW") have been read in. If a negative judgment is made at Step SB1, the control of the CPU 29 waits until a positive judgment is made at Step SB1.

On the other hand, if a positive judgment is made at Step SB1, the control of the CPU 29 goes to Step SB2 to add one to a number counted by a timer counter CT. Step SB2 is followed by Step SB3 to judge whether the number counted by the timer counter CT is equal to, or greater than, a predetermined reference time $T_0$. This reference time $T_0$ is equal to each predetermined time interval that is subjected to a frequency analysis carried out at Step SB4 described below. For example, the reference time $T_0$, i.e., the predetermined time interval may be equal to a multiple of a time equal to a full respiration period $T_{RE}$, or half the period $T_{RE}$, of the patient, e.g., a multiple of a time equal to four or two times each measured pulse period value RR of the patient.

Since, initially, a negative judgment is made at Step SB3, the control of the CPU 29 skips Steps SB4 to SB8 and goes to Step SB9. Meanwhile, if a positive judgment is made at Step SB3, the control goes to Steps SB4 to SB6 corresponding to the blood-oxygen-saturation calculating means 96. At Step SB4 corresponding to the frequency-analysis means, the CPU 29 applies the previously-described frequency analysis to each of the predetermined time intervals of each of the two PPW signals $SM_R$, $SM_{IR}$, and determines, for each time interval, an alternating-current component (signal power) $AC_R$ and a direct-current component $DC_R$ of the first PPW signal $SM_R$, and an alternating-current component $AC_{IR}$ and a direct-current component $DC_{IR}$ of the second PPW signal $SM_{IR}$.

Step SB4 is followed by Step SB5 corresponding to the ratio calculating means. At Step SB5, the CPU 29 calculates the ratio of the component $AC_R$ to the component $DC_R$ for the first signal $SM_R$ and the ratio of the component $AC_{IR}$ to the component $DC_{IR}$ for the second signal $SM_{IR}$, based on the components $AC_R$, $DC_R$ of the signal $SM_R$ and the components $AC_{IR}$, $DC_{IR}$ of the signal $SM_{IR}$ calculated at Step SB4.

At Step SB6, the CPU 29 calculates a blood oxygen saturation value $SaO_2$ of the patient, based on the ratio of the ratio of $AC_R$ to $DC_R$ to the ratio of $AC_{IR}$ to $DC_{IR}$, i.e., $R=(AC_R/DC_R)/(AC_{IR}/DC_{IR})$, according to the predetermined relationship between ratio R and saturation $SaO_2$, i.e., the expression (4).

Step SB6 is followed by Step SB7 where the CPU 29 judges whether the blood oxygen saturation value $SaO_2$ calculated at Step SB6 is smaller than a predetermined reference value, e.g., 90%. If a negative judgment is made at Step SB7, the control of the CPU 29 skips Step SB8 and goes to Step SB9. On the other hand, if a positive judgment is made at Step SB7, this decrease of the blood oxygen saturation $SaO_2$ may be followed by a decrease of the BP of the patient. Hence, the control goes to Step SB8 corresponding to the condition changing means 98. At Step SB8, the CPU 29 changes, based on the difference between the predetermined reference value (e.g., 90%) and the oxygen saturation value $SaO_2$ calculated at Step SB5, the predetermined reference range (e.g., from −25% to +25%) employed at Step SB11, to a changed reference range represented by a straight line shown in the graph of FIG. 11. The straight line defines a relationship between the above-indicated difference and the changed reference range. The straight line has a negative slope, and accordingly the width of the changed reference range linearly decreases from 25% as the oxygen saturation value $SaO_2$ calculated at Step SB6 decreases from 90%. Step SB8 is followed by Step SB9.

Step SB9 corresponding to the PWP-relating-information obtaining means 74. At Step SB9, the CPU 29 calculates a PWP time value $DT_{RP}$ and a PWP velocity value $V_M$ based on the R-wave of the waveform of each pulse of the ECG pulse wave and the rising point of the waveform of a corresponding pulse of the PPW which have been read in at Step SB1, in the same manner as that employed at Step SA2.

Step SB9 is followed by Step SB10 corresponding to the estimated-BP determining means 78. At Step SB10, the CPU 29 determines an estimated BP value EBP (i.e., an estimated systolic, mean, or diastolic BP value), based on the PWP time value $DT_{RP}$ or the PWP velocity value $V_M$ calculated at Step SB9, according to the relationship determined at Step SA6 at the time of the last BP measuring operation. Further, the CPU 29 displays, on the display device 32, a trend graph of the estimated BP values EBP which have been determined for successive pulses of the ECG pulse wave and the PPW and which include the "current" estimated BP value EBP determined in the current control cycle.

Step SB10 is followed by Step SB11 to start a BP measurement of the BP measuring means 70, when the estimated BP value EBP is judged as being abnormal and simultaneously at least one of the measured pulse period value RR and the calculated pulse-wave area value VR is judged as being abnormal, as a result of the execution of the BP-measurement-start judging routine of FIG. 12. Step SB11 corresponds to the BP-measurement starting means 86.

At Step SC1 of the flow chart of FIG. 12, the CPU 29 measures a pulse period value RR based on the time interval between a pair of successive pulses of the ECG pulse wave detected by the ECG-pulse-wave detecting device 34. Step SC1 corresponds to the pulse-period measuring means 82. Step SC1 is followed by Step SC2 corresponding to the RR-abnormality judging means 88. At Step SC2, the CPU 29 judges whether the measured pulse period value RR is abnormal. For instance, the CPU 29 judges that the pulse period value RR is abnormal when the state in which the pulse period value RR measured at Step SC1 in each control cycle is, by not less than a predetermined amount or a predetermined ratio (e.g., 5%), greater or smaller than the "control" pulse period value RR measured at the time of the last BP measuring operation has continued for a time period corresponding to not less than a predetermined number of pulses (e.g., 20 pulses). If a negative judgment is made at Step SC2, the control of the CPU 29 skips Step SC3 and goes to Step SC4. On the other hand, if a positive judgment is made at Step SC2, the control goes to Step SC3 where an RR flag is set "ON" so as to indicate the abnormality of the pulse period value RR.

Step SC3 is followed by Step SC4 to calculate a normalized pulse-wave area value VR based on the waveform of a pulse of the PPW detected by the probe 38. Step SC4 corresponds to the pulse-wave area calculating means 84. Step SC4 is followed by Step SC5 to judge whether the PPW signal $SM_3$ detected from the peripheral portion (i.e., finger) of the patient is normal. At Step SC5, the CPU 29 removes an abnormal waveform from the PPW signal $SM_3$. For example, the CPU 29 removes the waveform of each pulse of the PPW, if the inclination of base line of the waveform of each pulse is greater than a predetermined reference angle, or if the waveform has deformed due to a calibration of the monitoring apparatus 8. If a negative judgment is made at Step SC5, the control of the CPU 29 goes to Step SC10. On the other hand, if a positive judgement is made at Step SACS, the control of the CPU 29 goes to Step SC6.

At Step SC6 corresponding to the VR-abnormality judging means 89, the CPU 29 judges whether the normalized pulse-wave area value VR calculated at Step SC4 is abnormal. For instance, the CPU 29 judges the pulse-wave area value VR is abnormal when the state in which the pulse-wave area value VR calculated at Step SC4 in each control cycle is, by not less than a predetermined amount or a predetermined ratio (e.g., 3%), greater or smaller than the "control" pulse-wave area value VR calculated at the time of the last BP measuring operation has continued for a time period corresponding to not less than a predetermined number of pulses (e.g., 20 pulses). If a negative judgment is made at Step SC6, the control of the CPU 29 goes to Step SC8. On the other hand, if a positive judgment is made at Step SC6, the control of the CPU 29 goes to Step SC7 where a VR flag is set "ON" so as to indicate the abnormality of the pulse-wave area value VR.

Next, Step SC7 is followed by Step SC8 corresponding to the EBP-abnormality judging means 87. At Step SC8, the CPU 29 judges whether the estimated BP value EBP determined at Step SB10 is abnormal. For instance, the CPU 29 judges that the estimated BP value EBP determined at Step SB10 is abnormal when the state in which the estimated BP value EBP in each control cycle is, by not less than a predetermined amount or a predetermined ratio (e.g., 25%), greater or smaller than the "control" estimated BP value EBP determined at the time of the last BP measuring operation has continued for a time period corresponding to not less than a predetermined number of pulses (e.g., 20 pulses). If a negative judgment is made at Step SC8, the control of the CPU 29 goes to Step SC10. On the other hand, if a positive judgment is made at Step SC8, the control of the CPU 29 goes to Step SC9 where an EBP flag is set "ON" so as to indicate the abnormality of the estimated BP value EBP.

Step SC9 is followed by Step SC10 to judge whether the EBP flag is "ON" and simultaneously at least one of the RR flag and the VR flag is "ON". If a negative judgment is made at Step SC10, the control of the CPU 29 goes to Step SB12 corresponding to the period judging means 90. At Step SB12, the CPU 29 judges whether the predetermined period $T_{BP}$ (e.g., 20 minutes), that is, the calibration period, has passed after the last BP measuring operation was carried out at Step SA5 of FIG. 7. If a negative judgment is made at Step SB12, the control of the CPU 29 goes back to Step SB1 and the following steps so as to carry out the EBP determining routine, that is, determine an estimated BP value EBP for each of successive heartbeat-synchronous pulses, and display, on the display device 32, the trend graph of the determined estimated BP values EBP. On the other hand, if a positive judgment is made at Step SB12, the control of the CPU 29 goes back to the BP measuring routine of FIG. 7 so as to determine a new relationship between PWP-relating information and estimated BP value EBP.

Meanwhile, if a positive judgment is made at Step SC10, the control of the CPU 29 goes to Step SB13 of FIG. 10. At Step SB13, the CPU 29 displays the abnormality of the estimated-BP value EBP on the display device 32. Then, the control of the CPU 29 goes back to the BP measuring routine of FIG. 7 so as to start a BP measurement using the inflatable cuff 10 and determine a new relationship between PWP-relating information and estimated BP value EBP.

In the present embodiment, the index-value calculating means 92 calculates the index value $I_a$ indicative of the hardness of the blood vessel of the patient based on the BP values measured by the BP measuring means 70, and the condition changing means 98 changes, when the index value $I_a$ does not fall within the predetermined normal index-value range, the predetermined reference range (e.g., from −25% to +25%) employed by the EBP-abnormality judging means 87 at Step SC8, to the changed reference range (e.g., from −20% to +20%) which is contained in the predetermined reference range and is narrower than the same. Since the changed reference range is narrower than the predetermined reference range, the BP-measurement starting means 86 can earlier start a BP measurement of the BP measuring means 70. Therefore, in the case where the blood vessel of the patient has lost its flexibility or elasticity and accordingly becomes too hard, or has excessively largely expanded and accordingly becomes too soft, the present BP monitoring apparatus 8 can earlier measure an accurate and reliable BP value of the patient using the inflatable cuff 10.

In addition, the index-value calculating means 92 calculates the index value $I_a$ indicative of the hardness of the blood vessel of the patient based on the BP values measured by the BP measuring means 70, the change-value calculating means 94 calculates the change value $\Delta I_a$ of the index value $I_a$, and the condition changing means 98 changes, when the change value $\Delta I_a$ (absolute value) is greater than the predetermined reference value, the predetermined reference range employed by the EBP-abnormality judging means 87 at Step SC8, to the changed reference range narrower than the predetermined reference range. Since the changed reference range is narrower than the predetermined reference range, the BP-measurement starting means 86 can earlier start a BP measurement of the BP measuring means 70. Therefore, in the case where the hardness of the blood vessel of the patient has significantly changed and accordingly the estimated BP value EBP has lost its accuracy, the present BP monitoring apparatus 8 can earlier measure an accurate and reliable BP value of the patient using the cuff 10.

In the present embodiment, the blood-oxygen-saturation calculating means 96 calculates the blood oxygen saturation value $SaO_2$ of the peripheral body portion (e.g., finger) of the patient, based on the PPW, i.e., peripheral pulse wave detected by the PPW detecting probe 38, and the condition changing means 98 changes, when the calculated blood oxygen saturation value $SaO_2$ is smaller than the predetermined reference value (e.g., 90%), the predetermined reference range employed at Step SC8, to the changed reference range which is narrower than the predetermined reference range and is determined based on the difference between the calculated blood oxygen saturation value $SaO_2$ and the predetermined reference value. Accordingly, the BP-measurement starting means 86 can earlier start a BP measurement of the BP measuring means 70, by a time corresponding to the degree of abnormality of the calculated blood oxygen saturation value $SaO_2$, when the blood oxygen saturation value $SaO_2$ of the peripheral body portion of the patient has decreased prior to the change of BP of the patient because the hardness of the blood vessel of the patient has largely changed. Thus, the BP measuring means 70 can earlier measure an accurate and reliable BP value of the patient using the cuff 10.

The present BP monitoring apparatus 8 includes the BP-measurement starting means 86 which periodically starts a BP-measurement of the BP measuring means 70 at the predetermined period $T_{BP}$, and the period changing means 100 which changes, when the systolic BP value $BP_{SYS}$ measured by the BP measuring means 70 is smaller than the predetermined alarm value AL (e.g., 80 mmHg), the predetermined period $T_{BP}$ to the shorter period $T_{BP}'$, so that the starting means 86 can start a BP-measurement of the BP measuring means 70 at the changed, short period $T_{BP}'$. Therefore, the BP measuring means 70 can earlier measure an accurate and reliable BP value of the patient using the cuff 10.

While the present invention has been described in its preferred embodiment by reference to the drawings, it is to be understood that the invention may otherwise be embodied.

While in the illustrated embodiment the BP-measurement starting 86 starts a BP measurement of the BP measuring means 70, when it is judged at Step SC10 that the EBP flag is ON and at least one of the RR flag and the VR flag is ON. However, the BP-measurement starting 86 may be adapted to start a BP measurement of the BP measuring means 70, when it is judged at Step SC10 that at least one of the EBP flag, the RR flag, and the VR flag is ON.

At Step SC9, the EBP flag may be set ON only if it is judged at Step SC8 that a single estimated BP value EBP determined in each control cycle is, by not less than the predetermined ratio (e.g., 25%), greater or smaller than the "control" estimated BP value EBP determined at the time of the last BP measuring operation. This may apply to Steps SC2 and SC3, and Steps SC6 and SC7.

At Steps SC8 and SC9, the parameter $DT_{RP}$, $V_M$ may be employed in place of the parameter EBP, because each value $DT_{RP}$, $V_M$ corresponds to each value EBP, one by one, as defined by the second or third expression (2), (3).

While in the illustrated embodiment the index-value calculating means 92 calculates, at Step SA9 of the BP measuring routine of FIG. 7, the index value $I_a$ by dividing the pulse pressure $P_M$ by the measured mean BP value $BP_{MEAN}$, the index-value calculating means 92 may calculate an index value $I_a$ by dividing the PWP velocity value $V_M$, or the inverse, $1/DT_{RP}$, of the PWP time value $DT_{RP}$, by the systolic, mean, or diastolic BP value $BP_{SYS}$, $BP_{MEAN}$, $BP_{DIA}$ measured at Step SA5. In the latter case, since the index value $I_a$ is calculated based on the PWP-relating information $V_M$, $DT_{RP}$ that is used for determining the estimated BP values EBP of the patient, the index value $I_a$ and the change value $\Delta I_a$ enjoy the accuracy of the PWP-relating information $V_M$, $DT_{RP}$.

Although in the illustrated embodiment the period changing means 100 changes the predetermined period $T_{BP}$ to the short period $T_{BP}'$ when the systolic BP value $BP_{SYS}$ measured by the BP measuring means 70 is lower than the predetermined alarm value $AL_{SYS}$, the period changing means 100 may change the predetermined period $T_{BP}$ to the short period $T_{BP}'$ when the mean or diastolic BP value $BP_{MEAN}$, $BP_{DIA}$ measured by the BP measuring means 70 is lower than a corresponding predetermined alarm value $AL_{MEAN}$, $AL_{DIA}$.

In the illustrated embodiment, the relationship determining means 76 determines the relationship represented by the second or third expression (2) or (3). However, since each of the pulse period value RR and the pulse-wave area value VR relates to the BP of the patient, the relationship determining means 76 may determine a relationship represented by the following fifth expression (5):

$$EDP = \alpha VM + \beta RR + \gamma VR + \delta \tag{5}$$

where $\alpha$, $\beta$, $\gamma$, and $\delta$ are constants.

In the illustrated embodiment, the condition changing means 98 changes, at Step SB8 of the flow chart of FIG. 10, the predetermined reference range employed at Step SB11, to the changed reference range whose width decreases as the difference between the calculated blood oxygen saturation value $SaO_2$ and the predetermined reference value increases. However, the condition changing means 98 may change the predetermined reference range employed at Step SB11, to a changed reference range which is inverse-proportional to the difference between the calculated blood oxygen saturation value $SaO_2$ and the predetermined reference value.

In the illustrated embodiment, the pulse period RR (sec) may be replaced with heart rate HR (1/min), because the heart rate HR corresponds to the pulse period RR, one to one, according to the following expression: HR=60/RR.

It is to be understood that the present invention may be embodied with other changes and modifications that may occur to those skilled in the art without departing from the scope of the invention.

What is claimed is:

1. A blood-pressure monitoring apparatus comprising:
    a measuring device which includes an inflatable cuff adapted to apply a pressing pressure to a body portion of a living subject and which measures at least one blood-pressure value of the living subject by changing the pressing pressure of the inflatable cuff;
    a pulse-wave-propagation-relating-information obtaining device which iteratively obtains a piece of pulse-wave-propagation-relating information relating to propagation of a pulse wave through an arterial vessel of the living subject;
    estimating means for iteratively estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure;
    starting means for starting, when a value based on the estimated blood-pressure value does not fall within a predetermined first range, a blood-pressure measurement of the measuring device;
    index-value calculating means for calculating, based on said at least one blood-pressure value of the living subject measured by the measuring device, an index value indicative of a hardness of a blood vessel of the living subject; and
    range changing means for changing, when the calculated index value does not fall within a predetermined second range, the predetermined first range to a changed first range which is contained in the predetermined first range and is narrower than the predetermined first range.

2. An apparatus according to claim 1, further comprising relationship determining means for determining the relationship between pulse-wave-propagation-relating information and blood pressure, based on at least one blood-pressure value of the living subject measured by the measuring device and at least one piece of pulse-wave-propagation-relating information obtained by the pulse-wave-propagation-relating information obtaining device.

3. A blood-pressure monitoring apparatus comprising:
    a measuring device which includes an inflatable cuff adapted to apply a pressing pressure to a body portion of a living subject and which measures at least one blood-pressure value of the living subject by changing the pressing pressure of the inflatable cuff;
    a pulse-wave-propagation-relating-information obtaining device which iteratively obtains a piece of pulse-wave-propagation-relating information relating to propagation of a pulse wave through an arterial vessel of the living subject;
    estimating means for iteratively estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure;

starting means for starting, when a value based on to the estimated blood-pressure value does not fall within a predetermined first range, a blood-pressure measurement of the measuring device;

index-value calculating means for calculating, based on said at least one blood-pressure value of the living subject measured by the measuring device, an index value indicative of a hardness of a blood vessel of the living subject;

change-value calculating means for calculating a change value relating to a change of a first index value calculated by the index-value calculating means from a second index value calculated prior to the first index value by the index-value calculating means; and range changing means for changing, when the calculated change value does not fall within a predetermined second range, the predetermined first range to a changed first range which is contained in the predetermined first range and is narrower than the predetermined first range.

4. A blood-pressure monitoring apparatus comprising:

a measuring device which includes an inflatable cuff adapted to apply a pressing pressure to a first body portion of a living subject and which measures at least one blood-pressure value of the living subject by changing the pressing pressure of the inflatable cuff;

a pulse-wave-propagation-relating-information obtaining device which iteratively obtains a piece of pulse-wave-propagation-relating information relating to propagation of a pulse wave through an arterial vessel of the living subject;

estimating means for iteratively estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure;

starting means for starting, when a value based on the estimated blood-pressure value does not fall within a predetermined range, a blood-pressure measurement of the measuring device;

a photoelectric-pulse-wave obtaining device which is adapted to be worn on a second body portion of the living subject, and which emits, toward the second body portion, a first light exhibiting different absorption factors with respect to oxygenated hemoglobin and reduced hemoglobin, respectively, and a second light exhibiting substantially same absorption factors with respect to the oxygenated hemoglobin and the reduced hemoglobin, respectively, and obtains a first and a second photoelectric pulse wave from the first and second lights received from the second body portion, respectively;

blood-oxygen-saturation calculating means for calculating, based on the obtained first and second photoelectric pulse waves, a blood oxygen saturation value of the second body portion of the living subject; and range changing means for changing, when the calculated blood oxygen saturation value is smaller than a predetermined value, the predetermined range to a changed range which is contained in the predetermined range and is narrower than the predetermined range, the range changing means determining the changed range based on a difference between the calculated blood oxygen saturation value and the predetermined value.

5. A blood-pressure monitoring apparatus comprising:

a measuring device which includes an inflatable cuff adapted to apply a pressing pressure to a first body portion of a living subject and which measures at least one blood-pressure value of the living subject by changing the pressing pressure of the inflatable cuff;

blood-pressure-relating-value calculating means for iteratively calculating a blood-pressure-relating value relating to the blood pressure of the living subject;

starting means for starting, when a value based on the calculated blood-pressure-relating value satisfies a predetermined first condition, a blood-pressure measurement of the measuring device;

a circulatory-system-relating information obtaining device which obtains a circulatory-system-relating information relating to a circulatory system of the living subject; and condition changing means for changing, when the obtained circulatory-system-relating information satisfies a predetermined second condition, the predetermined first condition to a changed first condition which at least one of respective values based on a plurality of blood-pressure-relating values calculated by the blood-pressure-relating-value calculating means earlier satisfies than satisfying the predetermined first condition so that the starting means earlier starts the blood-pressure measurement of the measuring device.

6. An apparatus according to claim 5, wherein the blood-pressure-relating-value calculating means comprises at least one of pulse-period calculating means for iteratively calculating, as the calculated blood-pressure-relating value, a pulse period equal to a time interval between each pair of successive heartbeat-synchronous pulses of a pulse wave obtained from the living subject, and pulse-wave-area-relating-value calculating means for iteratively calculating, as the calculated blood-pressure-relating value, a pulse-wave-area-relating value relating to an area of each of a plurality of heartbeat-synchronous pulses of a pulse wave obtained from the living subject.

7. An apparatus according to claim 5, wherein the blood-pressure-relating-value calculating means comprises at least one of an electrocardiographic-pulse-wave detecting device which includes a plurality of electrodes adapted to be put on a plurality of portions of the living body and detects an electrocardiographic pulse wave including a plurality of heartbeat-synchronous pulses, from the subject via the electrodes, and a photoelectric-pulse-wave detecting device which is adapted to be worn on a second body portion of the living subject, and which emits a light toward the second body portion and obtains a photoelectric pulse wave including a plurality of heartbeat-synchronous pulses, from the light received from the second body portion.

8. An apparatus according to claim 5, wherein the starting means comprises means for starting, when the calculated blood-pressure-relating value satisfies the predetermined first condition, the blood-pressure measurement of the measuring device.

9. An apparatus according to claim 5, wherein the starting means comprises:

means for calculating, as the value based on the calculated blood-pressure-relating value, a change value relating to a change of a first blood-pressure-relating value calculated by the blood-pressure-relating-value calculating means from a second blood-pressure-relating value calculated prior to the first calculated blood-pressure-relating value by the blood-pressure-relating-value calculating means; and means for starting, when the calculated change value satisfies the predetermined first condition, the blood-pressure measurement of the measuring device.

10. An apparatus according to claim 5, further comprising an informing device which informs, when the value based on the calculated blood-pressure-relating value satisfies the predetermined first condition, a user of an occurrence of an abnormality to the living subject.

11. An apparatus according to claim 5, wherein the starting means comprises means for starting the blood-pressure measurement of the measuring device, when the value based on the calculated blood-pressure-relating value satisfies the predetermined first condition selected from the group consisting of (a) the value based on the calculated blood-pressure-relating value does not fall within a predetermined first range, (b) the value based on the calculated blood-pressure-relating value is greater than a predetermined first value, and (c) the value based on the calculated blood-pressure-relating value is smaller than a predetermined second value.

12. An apparatus according to claim 11, wherein the condition changing means comprises means for changing the predetermined first condition to the changed first condition selected from the group consisting of (d) said at least one of the respective values based on the plurality of blood-pressure-relating values does not fall within a changed first range which is contained in the predetermined first range and is narrower than the predetermined first range, (e) said at least one of the respective values based on the plurality of blood-pressure-relating values is greater than a changed first value smaller than the predetermined first value, and (f) said at least one of the respective values based on the plurality of blood-pressure-relating values is smaller than a changed second value greater than the predetermined second value.

13. An apparatus according to claim 12, wherein the circulatory-system-relating-information obtaining device comprises index-value calculating means for calculating, based on said at least one blood-pressure value of the living subject measured by the measuring device, an index value indicative of a hardness of a blood vessel of the living subject, and wherein the condition changing means comprises means for changing the predetermined first condition to the changed first condition, when the calculated index value satisfies the predetermined second condition selected from the group consisting of (g) the calculated index value does not fall within a predetermined second range, (h) the calculated index value is greater than a predetermined third value, and (i) the calculated index value is smaller than a predetermined fourth value.

14. An apparatus according to claim 13, wherein the blood-pressure-relating value calculating means comprises:

a pulse-wave-propagation-relating-information obtaining device which iteratively obtains a piece of pulse-wave-propagation-relating information relating to propagation of a pulse wave through an arterial vessel of the living subject; and estimating means for estimating a blood-pressure value of the living subject, based on each piece of pulse-wave-propagation-relating information of a plurality of pieces of pulse-wave-propagation-relating information obtained by the pulse-wave-propagation-relating-information obtaining device, according to a predetermined relationship between pulse-wave-propagation-relating information and blood pressure, and wherein the index-value calculating means comprises means for calculating the index value indicative of the hardness of the blood vessel of the living subject, based on the blood-pressure value of the subject measured by the measuring device and the piece of pulse-wave-propagation-relating information obtained by the pulse-wave-propagation-relating-information obtaining device when the blood-pressure value of the subject is measured by the measuring device.

15. An apparatus according to claim 12, wherein the circulatory-system-relating-information obtaining device comprises;

index-value calculating means for calculating, based on said at least one blood-pressure value of the living subject measured by the measuring device, an index value indicative of a hardness of a blood vessel of the living subject; and change-value calculating means for calculating a change value relating to a change of a first index value calculated by the index-value calculating means from a second index value calculated prior to the first index value by the index-value calculating means, and wherein the condition changing means comprises means for changing the predetermined first condition to the changed first condition, when the calculated change value satisfies the predetermined second condition selected from the group consisting of (g) the calculated change value does not fall within a predetermined second range, (h) the calculated change value is greater than a predetermined third value, and (i) the calculated change value is smaller than a predetermined fourth value.

16. An apparatus according to claim 12, wherein the circulatory-system-relating-information obtaining device comprises:

a photoelectric-pulse-wave obtaining device which is adapted to be worn on a second body portion of the living subject, and which emits, toward the second body portion, a first light exhibiting different absorption factors with respect to oxygenated hemoglobin and reduced hemoglobin, respectively, and a second light exhibiting substantially same absorption factors with respect to the oxygenated hemoglobin and the reduced hemoglobin, respectively, and obtains a first and a second photoelectric pulse wave from the first and second lights received from the second body portion, respectively; and blood-oxygen-saturation calculating means for calculating, based on the obtained first and second photoelectric pulse waves, a blood oxygen saturation value of the second body portion of the living subject; and wherein the condition changing means comprises means for changing the predetermined first condition to the changed first condition, when the calculated blood oxygen saturation value satisfies the predetermined second condition that the calculated blood oxygen saturation value is smaller than a predetermined third value.

17. An apparatus according to claim 16, wherein the condition changing means comprises:

means for changing, when the calculated blood oxygen saturation value is smaller than the predetermined third value, the predetermined first condition to the changed first condition that (d) said at least one of the respective values based on the plurality of blood-pressure-relating values does not fall within the changed first range; and means for determining the changed first range based on a difference between the calculated blood oxygen saturation value and the predetermined third value.

18. An apparatus according to claim 5, wherein the blood-pressure-measurement starting means comprises periodically starting means for periodically starting a blood-pressure measurement of the measuring device at a predetermined period.

19. An apparatus according to claim 18, further comprising period changing means for changing, when the blood-pressure value of the living subject measured by the measuring device is smaller than a reference value, the predetermined period to a changed period shorter than the predetermined period so that the periodically starting means starts a blood-pressure measurement of the measuring device at the changed period.

20. An apparatus according to claim 5, wherein the blood-pressure-relating-value calculating means comprises:

a pulse-wave-propagation-relating-information obtaining device which iteratively obtains a piece of pulse-wave-propagation-relating information relating to propagation of a pulse wave through an arterial vessel of the living subject;

relationship determining means for determining a relationship between pulse-wave-propagation-relating information and blood pressure, based on at least one blood-pressure value of the living subject measured by the measuring device and at least one piece of pulse-wave-propagation-relating information obtained by the pulse-wave-propagation-relating-information obtaining device; and estimating means for iteratively estimating, as the calculated blood-pressure-relating value, a blood-pressure value of the living subject, based on each piece of pulse-wave-propagation-relating information of a plurality of pieces of pulse-wave-propagation-relating information obtained by the pulse-wave-propagation-relating-information obtaining device, according to the determined relationship between pulse-wave-propagation-relating information and blood pressure.

21. An apparatus according to claim 20, wherein the pulse-wave-propagation-relating-information obtaining device comprises at least one of pulse-wave-propagation-time calculating means for iteratively calculating a pulse-wave propagation time which is needed for each of a plurality of heartbeat-synchronous pulses of the pulse wave to propagate between two portions of the arterial vessel of the living subject, and pulse-wave-propagation-velocity calculating means for iteratively calculating a pulse-wave propagation velocity at which each of a plurality of heartbeat-synchronous pulses of the pulse wave propagates between two portions of the arterial vessel of the living subject.

* * * * *